(12) United States Patent
Mehta et al.

(10) Patent No.: US 7,825,101 B2
(45) Date of Patent: Nov. 2, 2010

(54) MODULATION OF MLCK-L EXPRESSION AND USES THEREOF

(75) Inventors: Dolly Mehta, Elmhurst, IL (US); Shahid S. Siddiqui, Wilmette, IL (US); Asrar Malik, Hinsdale, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 12/439,370

(22) PCT Filed: Aug. 30, 2007

(86) PCT No.: PCT/US2007/077310

§ 371 (c)(1),
(2), (4) Date: Aug. 27, 2009

(87) PCT Pub. No.: WO2008/028085

PCT Pub. Date: Mar. 6, 2008

(65) Prior Publication Data

US 2010/0093830 A1    Apr. 15, 2010

Related U.S. Application Data

(60) Provisional application No. 60/841,000, filed on Aug. 30, 2006.

(51) Int. Cl.
*A61K 31/70* (2006.01)
*C07H 21/04* (2006.01)

(52) U.S. Cl. ........................................ 514/44; 536/24.5

(58) Field of Classification Search ........................ None
See application file for complete search history.

(56) References Cited

U.S. PATENT DOCUMENTS

2003/0143732 A1 * 7/2003 Fosnaugh et al. ............ 435/325
2005/0261196 A1 * 11/2005 Turner et al. .................. 514/16
2006/0058255 A1 * 3/2006 Chen et al. .................... 514/44

OTHER PUBLICATIONS

Lazar et al. Genomics 1999, vol. 57, pp. 256-267.*
Bass Nature 2001, vol. 411, pp. 428-429.*
Tinsley et al. Trends in Pharmacological Sciences 2004, vol. 25, pp. 64-66.*
Clayburgh, D.R, et al., A differentiation-dependent splice variant of myosin light chain kinase, MLCK1, regulates epithelial tight junction permeability, J. Biol. Chem., Dec. 31, 2004, vol. 279, No. 53, pp. 55506-55513.
Kim Min Tae, et al., Involvement of calmodulin and myosin light chain kinase in activation of mTRPC5 expressed in HEK cells. Amer. J Physiol.—Cell Physiol., Apr. 2006, vol. 290, No. 4, pp. C1031-C1040.
Wainwright, M.S., et al., Protein kinase involved in lung injury susceptibility: evidence from enzyme isoform genetic knockout and in vivo inhibitor treatment, Proc. Nat. Acad. Sci. USA, May 13, 2003, vol. 100, No. 10, pp. 6233-6238.
Gao Li, et al., Novel polymorphisms in the myosin light chain kinase gene confer risk for acute lung injury, Amer. J. Resp. Cell and Mol. Biol., Apr. 2006, vol. 34, No. 4, pp. 487-495.
Bonetta, L., et al., RNAi: Silencing never sounded better, Nature Methods, Oct. 2004, vol. 1, No. 1, pp. 79-85.

* cited by examiner

*Primary Examiner*—Tracy Vivlemore
(74) *Attorney, Agent, or Firm*—Teddy Scott, Jr.; Todd S. Hofmeister; Polsinelli Shughart PC

(57) ABSTRACT

In various aspects and embodiments the invention provides methods and reagents for controlling gene expression, and for treating disorders and diseases. Embodiments provide methods and reagents specifically for the regulation of MLCK expression and for the use thereof in treating disorders and diseases. Various embodiments provide methods and reagents for specifically down regulating the expression of MLCK-L more efficiently than that of MLCK-S, and for the use thereof in treating disorders and diseases. Embodiments provide siNA for the same, particularly siRNAs. Various of the embodiments are useful for the treatment of inflammatory disorders and diseases, including, for one example in this regard, Asthma.

4 Claims, 10 Drawing Sheets

Figure 1:
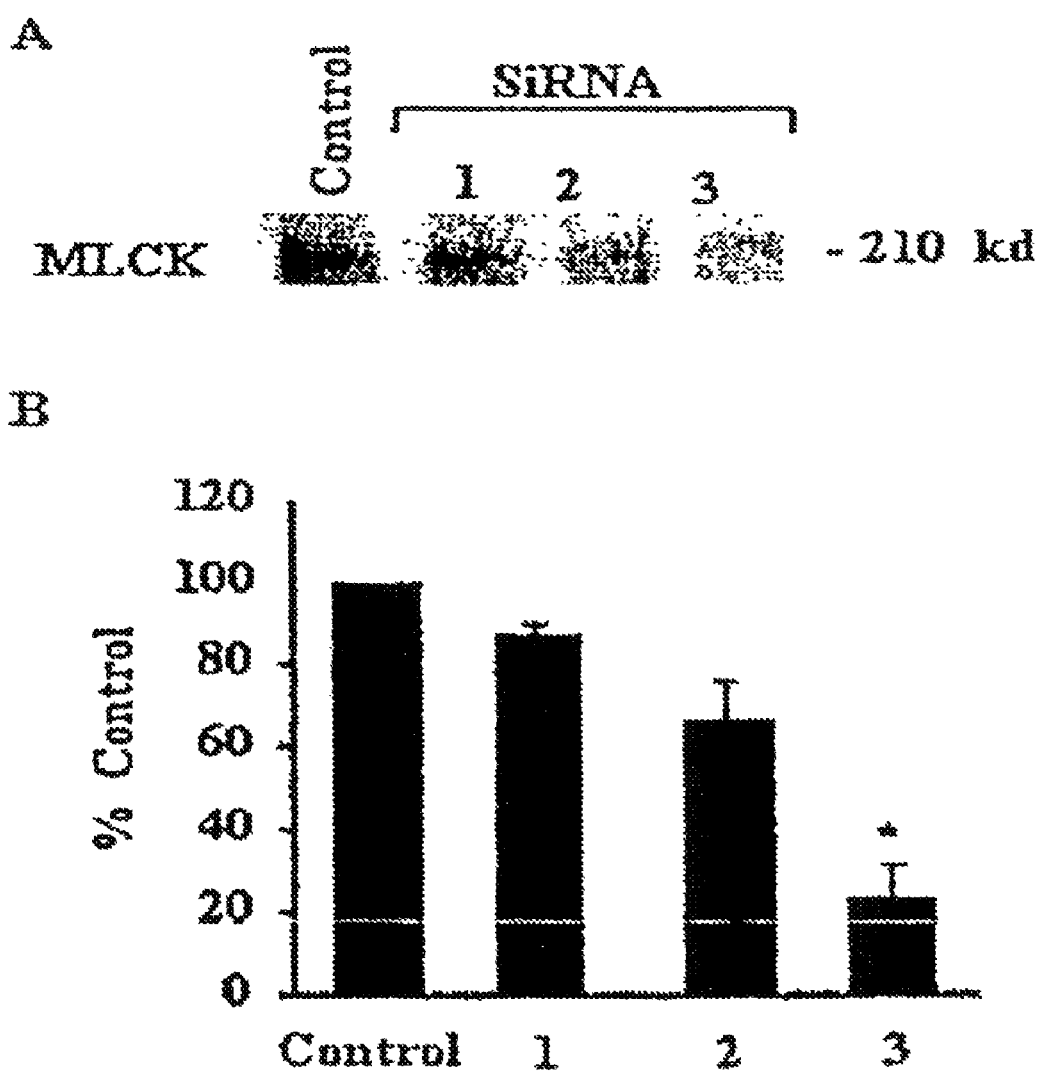

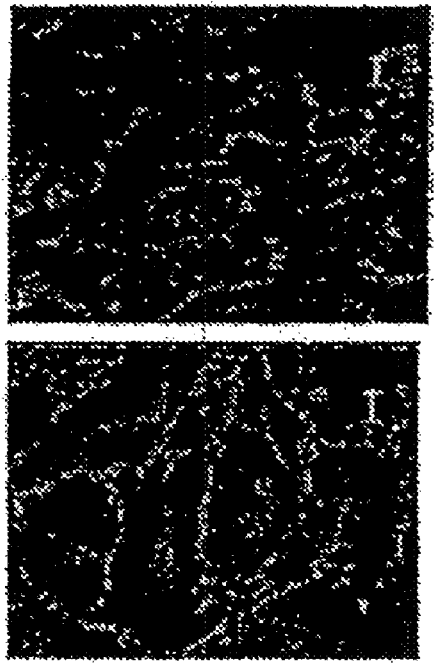
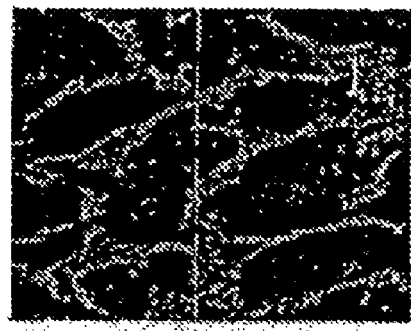
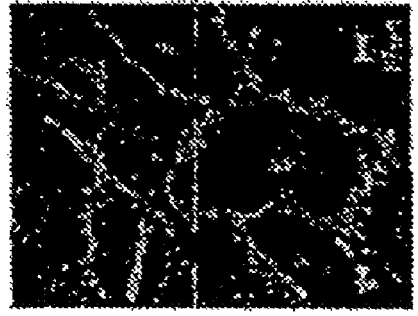
Figure 5

SEQUENCE LISTING

```
<160> NUMBER OF SEQ ID NOS: 4

<210> SEQ ID NO 1
<211> LENGTH: 21
<212> TYPE: RNA
<213> ORGANISM: Artificial
<220> FEATURE:
<223> OTHER INFORMATION: MLCK-L siRNA
<220> FEATURE:
<221> NAME/KEY: misc_feature
<222> LOCATION: (1)..(2)
<223> OTHER INFORMATION: n is a, c, g, or u

<400> SEQUENCE: 1
nnggacugcg cuguuauuga g                                              21

<210> SEQ ID NO 2
<211> LENGTH: 21
<212> TYPE: RNA
<213> ORGANISM: Artificial
<220> FEATURE:
<223> OTHER INFORMATION: MLCK-L siRNA
<220> FEATURE:
<221> NAME/KEY: misc_feature
<222> LOCATION: (1)..(2)
<223> OTHER INFORMATION: n is a, c, g, or u

<400> SEQUENCE: 2
nnguggaaag gcuugccgug a                                              21

<210> SEQ ID NO 3
<211> LENGTH: 21
<212> TYPE: RNA
<213> ORGANISM: Artificial
<220> FEATURE:
<223> OTHER INFORMATION: MLCK-L siRNA
<220> FEATURE:
<221> NAME/KEY: misc_feature
<222> LOCATION: (1)..(2)
<223> OTHER INFORMATION: n is a, c, g, or u

<400> SEQUENCE: 3
nnugggcagc ccauccagua c                                              21

<210> SEQ ID NO 4
<211> LENGTH: 4740
<212> TYPE: DNA
<213> ORGANISM: Homo sapiens
```

<400> SEQUENCE: 4

```
ccatggggga tgtgaagctg gttgcctcgt cacacatttc caaaacctcc ctcagtgtgg      60
atccctcaag agttgactcc atgcccctga cagaggcccc tgctttcatt ttgcccctc     120
ggaacctctg catcaaagaa ggagccaccg ccaagttcga agggcgggtc cggggttacc    180
cagagcccca ggtgacatgg cacagaaacg ggcaacccat caccagcggg ggccgcttcc    240
tgctggattg cggcatccgg gggactttca gccttgtgat tcatgctgtc catgaggagg    300
acagggaaa gtatacctgt gaagccacca atggcagtgg tgctcgccag gtgacagtgg     360
agttgacagt agaaggaagt tttgcgaagc agcttggtca gcctgttgtt ccaaaacct    420
taggggatag atttcagct tcagcagtgg agacccgtcc tagcatctgg ggggagtgcc     480
caccaaagtt tgctaccaag ctgggccgag ttgtggtcaa agaaggacag atgggacgat     540
tctcctgcaa gatcactggc cggccccaac cgcaggtcac ctggctcaag ggaaatgttc     600
cactgcagcc gagtgcccgt gtgtctgtgt ctgagaagaa cggcatgcag gttctggaaa     660
tccatggagt caaccaagat gacgtgggag tgtacacgtg cctggtggtg aacgggtcgg     720
ggaaggcctc gatgtcagct gaactttcca tccaaggttt ggacagtgcc aataggtcat     780
ttgtgagaga aacaaaagcc accaattcag atgtcaggaa agaggtgacc aatgtaatct     840
caaaggagtc gaagctggac agtctggagg ctgcagccaa agcaagaac tgctccagcc      900
cccagagagg tggctcccca ccctgggctg caaacagcca gcctcagccc caagggagt      960
ccaagctgga gtcatgcaag gactcgccca gaacggcccc gcagacccg gtccttcaga     1020
agacttccag ctccatcacc ctgcaggccg caagagttca gccggaacca agagcaccag    1080
gcctgggggt cctatcacct tctggagaag agaggaagag gccagctcct ccccgtccag    1140
ccaccttccc caccaggcag cctggcctgg ggagccaaga tgttgtgagc aaggctgcta    1200
acaggagaat ccccatggag ggccagaggg attcagcatt ccccaaattt gagagcaagc    1260
cccaaagcca ggaggtcaag gaaaatcaaa ctgtcaagtt cagatgtgaa gtttccggga    1320
ttccaaagcc tgaagtggcc tggttcctgg aaggcacccc cgtgaggaga caggaaggca    1380
gcattgaggt ttatgaaaat gctggctccc attacctctg cctgctgaaa gcccggacca    1440
gggacagtgg gacatacagc tgcactgctt ccaacgccca aggccaggtg tcctgtagct    1500
ggaccctcca agtggaaagg cttgccgtga tggaggtggc cccctccttc tccagtgtcc    1560
tgaaggactg cgctgttatt gagggccagg attttgtgct gcagtgctcc gtacggggga    1620
ccccagtgcc ccggatcact tggctgctga atgggcagcc catccagtac gctcgctcca    1680
cctgcgaggc cggcgtggct gagctccaca tccaggatgc cctgccggag gaccatggca    1740
cctacacctg cctagctgag aatgccttgg ggcaggtgtc ctgcagcgcc tgggtcaccg    1800
tccatgaaaa gaagagtagc aggaagagtg agtaccttct gctgtggct cccagcaagc     1860
ccactgcacc catcttcctg cagggcctct ctgatctcaa agtcatggat ggaagccagg    1920
tcactatgac tgtccaagtg tcagggaatc caccccctga agtcatctgg ctgcacaatg    1980
ggaatgagat ccaagagtca gaggacttcc actttgaaca gagaggaact cagcacagcc    2040
tttgtatcca ggaagtgttc ccggaggaca cgggcacgta cacctgcgag gcctggaaca    2100
gcgctggaga ggtccgcacc caggccgtgc tcacggtaca agagcctcac gatggcaccc    2160
agccctggtt catcagtaag cctcgctcag tgacagcctc cctgggccag agtgtcctca    2220
tctcctgcgc catagctggt gacccctttc ctaccgtgca ctggctcaga gatggcaaag    2280
```

```
ccctctgcaa agacactggc cacttcgagg tgcttcagaa tgaggacgtg ttcaccctgg    2340
ttctaaagaa ggtgcagccc tggcatgccg gccagtatga gatcctgctc aagaaccggg    2400
ttggcgaatg cagttgccag gtgtcactga tgctacagaa cagctctgcc agagcccttc    2460 cacggggag ggagcctgcc agctgcgagg acctctgtgg tggaggagtt ggtgctgatg     2520
gtggtggtag tgaccgctat gggtccctga ggcctggctg ccagcaaga gggcagggtt     2580 ggctagagga ggaagacggc gaggacgtgc gagggtgct gaagaggcgc gtggagacga     2640
ggcagcacac tgaggaggcg atccgccagc aggaggtgga gcagctggac ttccgagacc    2700
tcctggggaa gaaggtgagt acaaagaccc tatcggaaga cgacctgaag gagatcccag    2760
ccgagcagat ggatttccgt gccaacctgc aacggcaagt gaagccaaag actgtgtctg    2820
aggaagagag gaaggtgcac agcccccagc aggtcgattt tcgctctgtc ctggccaaga    2880
aggggacttc caagaccccc gtgcctgaga aggtgccacc gccaaaacct gccaccccgg    2940
attttcgctc agtgctgggt ggcaagaaga aattaccagc agagaatggc agcagcagtg    3000
ccgagaccct gaatgccaag gcagtggaga gttccaagcc cctgagcaat gcacagcctt    3060
cagggccctt gaaacccgtg gcaacgcca agcctgctga cccctgaag ccaatgggca     3120 acgccaagcc tgccgagacc ctggagccca tgggcaatgc caagcctgat gagaaccaat    3180
aatccgctag caaagaagaa ctcaagaaag acgttaagaa tgatgtgaac tgcaagagag    3240
gccatgcagg gaccacagat aatgaaaaga gatcagagag ccaggggaca gccccagcct    3300
tcaagcagaa gctgcaagat gttcatgtgg cagagggcaa gaagctgctg ctccagtgcc    3360
aggtgtcttc tgaccccccca gccaccatca tctggacgct gaacggaaag accctcaaga    3420
ccaccaagtt catcatcctc tcccaggaag gctcactctg ctccgtctcc atcgagaagg    3480
cactgcctga ggacagaggc ttatacaagt gtgtagccaa gaatgacgct ggccaggcgg    3540
agtgctcctg ccaagtcact gtggatgatg ctccagccag tgagaacacc aaggccccag    3600
agatgaaatc ccggaggccc aagagctctc ttcctcccgt gctaggaact gagagtgatg    3660
cgactgtgaa aaagaaacct gcccccaaga cacctccgaa ggcagcaatg cccctcaga    3720 tcatccagtt ccctgaggac cagaaggtac gcgcaggaga gtcagtggag ctgtttggca    3780
aagtgacagg cactcagccc atcacctgta cctggatgaa gttccgaaag cagatccagg    3840
aaagcgagca catgaaggtg gagaacagcg agaatggcag caagctcacc atcctggccg    3900
cgcgccagga gcactgcggc tgctacacac tgctggtgga gaacaagctg ggcagcaggc    3960
aggcccaggt caacctcact gtcgtggata gccagacccc ccagctggc acaccttgtg     4020 cctctgacat tcggagctcc tcactgaccc tgtcctggta tggctcctca tatgatgggg    4080
gcagtgctgt acagtcctac agcatcgaga tctgggactc agccaacaag acgtggaagg    4140
aactagccac atgccgcagc acctctttca cgtccagga cctgctgcct gaccacgaat    4200
ataagttccg tgtacgtgca atcaacgtgt atggaaccag tgagccaagc caggagtctg    4260
aactcacaac ggtaggagag aaacctgaag agccgaagga tgaagtggag gtgtcagatg    4320
atgatgagaa ggagccccgag gttgattacc ggacagtgac aatcaatact gaacaaaaag    4380
tatctgactt ctacgacatt gaggagagat taggatctgg gaaatttgga caggtctttc    4440
gacttgtaga aaagaaaact cgaaaagtct gggcagggaa gttcttcaag gcatattcag    4500
caaaagagaa agagaatatc cggcaggaga ttagcatcat gaactgcctc caccccccta    4560
agctggtcca gtgtgtggat gcctttgaag aaaaggccaa catcgtcatg gtcctggaga    4620
```

```
tcgtgtcagg aggggagctg tttgagcgca tcattgacga ggactttgag ctgacggagc    4680
gtgagtgcat caagtacatg cggcagatct cggagggagt ggagtacatc cacaagcagg    4740
```

MODULATION OF MLCK-L EXPRESSION AND USES THEREOF

REFERENCE TO RELATED APPLICATIONS

This application claims full right of priority and is a continuation-in-part application of U.S. Provisional Application Ser. No. 60/841,000 filed on 30 Aug. 2006 which is herein incorporated by reference in its entirety.

BRIEF DESCRIPTION OF SEQUENCE LISTING

A sequence listing in accordance with 37 C.F.R. §§1.821-1.825 is attached to the present invention and contained in a file named "053839_01700_01USPC_ST25.txt" (6.89 Kb, created Jul. 20, 2009) and is hereby incorporated by reference.

FIELD OF THE INVENTION

In various aspects and embodiments the invention relates generally to the field of gene expression and its control, to reagents and methods therefore, and to the treatment of disorders and diseases thereby. Various embodiments relate to regulation of MLCK and to interfering nucleic acids therefore. Various embodiments relate to down-regulation of MLCK-L expression without concomitant down regulation of MLCK-S, to reagents and methods therefore, and to the treatment of disorders and diseases thereby.

BACKGROUND

Increased lung vascular permeability is a hallmark of acute respiratory distress syndrome (ARDS). It has been established that endothelium regulates passage of plasma proteins and other macromolecules across the vessel wall and performs the vital task of maintaining the integrity of the alveolar-capillary barrier. See Mehta and Malik, Physiol. Rev., January 2006; 86(1):279-367. Endothelial cells regulate the barrier properties of the microvessel wall by altering their shape, which was earlier described as "cell rounding" by Majno and Palade (1961). See Majno et al., J. Biophys. Biochem. Cytol., December, 1961: 11:571-605. Cell shape change occurs as a result of actinomyosin-based endothelial cell contraction, requiring myosin light chain (MLC) phosphorylation. See Mehta and Malik, Physiol. Rev., January 2006; 86(1):279-367. The phosphorylation of MLC is catalyzed by activated myosin light chain kinase (MLCK) in the presence of ionized intracellular calcium and calmodulin.[3] Several studies using either constitutively active MLCK or pharmacological inhibitors of MLCK have shown that MLCK-induced MLC phosphorylation plays an essential role in regulating endothelial permeability in vitro and in vivo.[3-10] In addition, studies indicate that increased MLCK activity and MLC phosphorylation in endothelial cell monolayers are required for transendothelial polymorphonuclear ("PMN") migration elicited by chemotactic agents.[11, 12] Importantly, recent gene expression profiling studies from several acute lung injury patients have identified SNPs (single-nucleotide polymorphisms) in the MLCK gene (MYLK) that may be associated with ARDS. MLCK is thus indicated to be a potential therapeutic target for treating ARDS.[13, 14]

Interestingly, primary endothelial cells are known to express the 210 kDa long isoform of MLCK referred to as endothelial MLCK-L and the well-known 130 kDa smooth muscle MLCK isoform (MLCK-S, as used herein).[9, 15-17] These isoforms are encoded from a single gene on chromosome 3. Structurally, MLCK-L contains all the domains present in the smooth muscle isoform, but in addition, has a unique 922-amino acid N-terminal domain containing consensus sites for phosphorylation by multiple protein kinases, including cAMP-dependent protein kinase A (PKA), PKC, PAK, Src, and $Ca^{2+}$/CaM-dependent protein kinase II.[1, 3] The N-terminus of MLCK-L has been shown to interact with Src.[3] Macrophage inhibitory factor[18] and microtubules[19] also bind with high affinity to the N-terminus of MLCK-L. Thus, regulation of MLCK-L by serine and tyrosine kinases, and its complexation with multiple proteins indicate that many signaling pathways may exert control on endothelial permeability by converging to MLCK-L. However, previous studies using approaches which target the kinase activity of MLCK without isoform specificity have not been clear in identifying the individual role of MLCK-L in regulating endothelial barrier function. In accordance with various aspects and embodiments of the invention herein disclosed an siRNA sequence that specifically "knocks down" MLCK-L in cultured cells was developed and used in a recently developed strain of mice lacking MLCK-L (MLCK210$^{-/-}$ mice)[6] to show the importance of MLCK210 in the mechanism of increased lung vascular permeability. A thrombin or a PAR-1 peptide agonist was used to elicit an endothelial permeability response because PAR-1 receptor agonists are known to increase endothelial permeability by actinomyosin induced contraction downstream of G-protein-coupled proteinase-activated receptor-1 (PAR-1) in endothelial monolayer as well as in vivo models.[1] The results show that, in accordance with the invention. MLCK-L is a key effector mediating the PAR-1-induced increase in lung vascular permeability in part through phosphorylation of MLC and MLCK is involved in regulation of calcium entry via a previously undescribed interaction with store operated channels.

SUMMARY

In various aspects and embodiments the invention provides new nucleic acid molecules which down regulate expression and/or stability of MLCK-L. In various aspects and embodiments the invention provides compounds and methods which are useful in molecular investigations of MLCK and, additionally, in the diagnosis, prevention, and therapy of tissue inflammation and angiogenesis. In embodiments the compounds are stable nucleic acid agents which may be used to knockdown or down regulate MLCK-L. In embodiments the nucleic acid agent is a siRNA. In embodiments, the nucleic acids are modified to adjust for single-nucleotide polymorphisms which may be reflected in the targeted DNA or RNA molecule(s).

Embodiments of the invention provide a double stranded short interfering nucleic acid (siNA) molecule that directs cleavage of a myosin light chain kinase (MLCK) RNA, wherein: (a) each strand of said siNA molecule is about 19 to about 25 nucleotides in length; and (b) one strand of said siNA molecule comprises a region having a nucleotide sequence having sufficient complementarity to the MLCK RNA for the siNA molecule to direct cleavage of the MLCK RNA via RNA interference. In embodiments the double-stranded siNA is a siRNA. In embodiments the siNA cleaves MLCK-L RNA more efficiently than MLCK-S RNA. In embodiments the siNA cleaves MLCK-L RNA at least twice as efficiently as it cleaves MLCK-S RNA. In embodiments the siNA specifically cleaves MLCK-L RNA and substantially does not cleave MLCK-S RNA. In embodiments, the siRNA comprises a region having the sequence of SEQ ID NO:3. In embodiments, the siNA is a siRNA.

Embodiments of the invention provide a method for modulating MLCK expression in a cell, comprising introducing into a cell a double stranded siNA that cleaves MLCK RNA, wherein (a) each strand of said siNA molecule is about 19 to about 25 nucleotides in length; and (b). one strand of said siNA molecule comprises a region having a nucleotide sequence having sufficient complementarity to the MLCK RNA for the siNA molecule to direct cleavage of the MLCK RNA via RNA interference. In embodiments the siNA specifically cleaves MLCK-L RNA and substantially does not cleave MLCK-S RNA. In embodiments, the siNA comprises a region having the sequence of SEQ ID NO:3. In embodiments the siNA is a siRNA.

Embodiments of the invention provide a method for modulating tissue inflammation of a patient suffering therefrom, comprising: administering to a patient suffering from tissue inflammation a nucleic acid in an amount and by a route effective to modulate said tissue inflammation, wherein said nucleic acid comprises a region complementary to an RNA encoded by an MLCK gene and is effective to direct cleavage specifically of said RNA by RNA interference. In embodiments the nucleic acid is a double stranded siNA. In embodiment the nucleic acid is a double stranded siNA that cleaves MLCK RNA. In embodiment each strand of said siNA molecule is about 19 to about 25 nucleotides in length; and one strand of said siNA molecule comprises a region having a nucleotide sequence having sufficient complementarity to the MLCK RNA for the siNA molecule to direct cleavage of the MLCK RNA via RNA interference. In embodiments the siNA specifically cleaves MLCK-L RNA and substantially does not cleave MLCK-S RNA. In embodiments, the siNA comprises a region having the sequence of SEQ ID NO:3. In embodiments, the siNA is a siRNA.

Embodiments of the invention provide a method for treating asthma in a patient suffering therefrom, comprising: administering to a patient suffering from asthma a nucleic acid in an amount and by a route effective to treat asthma, wherein said nucleic acid comprises a region complementary to an RNA encoded by an MLCK gene and is effective to direct cleavage specifically of said RNA by RNA interference. In embodiments the nucleic acid is a siNA. In embodiments the nucleic acid is a siNA that specifically cleaves MLCK-L RNA and substantially does not cleave MLCK-S RNA. In embodiments the nucleic acid comprises a region having the sequence of SEQ ID NO:3. In embodiments the nucleic acid is a siNA. In embodiments the nucleic acid is a siRNA.

In various embodiments the invention provides methods for modulating expression of genes in a patient comprising: administering to a patient a nucleic acid complementary to a target 3'UTR mRNA encoded by a gene expressed in the endothelium in an amount and by a route effective for modulating the activity of said mRNA in said patient. In embodiments in this regard the nucleic acid is a siNA. In embodiments the nucleic acid specifically cleaves MLCK RNAs. In embodiments the nucleic acid specifically cleaves MLCK-L RNA and substantially does not cleave MLCK-S RNA. In embodiments the nucleic acid is a siNA. In embodiments the nucleic acid is a siRNA. In embodiments the nucleic acid comprises a region complementary to a region of an MLCK RNA. In embodiments the region has greater complementary to MLCK-L than to MLCK-S RNA. In embodiments the region is complementary to all or a part of the sequence of nucleotides 1428 to 1634 of the sequence of human MLCK-L RNA, as set out in SEQ ID NO. 4. In embodiments the nucleic acid directs cleavage by RNA interference of MLCK specifically in non-smooth muscle cells but substantially not in smooth muscle cells. In embodiments the nucleic acid comprises a region having the sequence of SEQ ID NO:1, SEQ ID NO:2, or SEQ ID NO:3.

In embodiments the nucleic acid is effective to treat Sepsis, Acute Respiratory Distress Syndrome, Trauma, Inflammation and/or Asthma.

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is commonly referred to as post-transcriptional gene silencing or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898, 031; Clemens et al., 1997, J. Interferon & Cytokine Res., 17, 503-524; Adah et al., 2001, Curr. Med. Chem., 8, 1189).

In particular, the instant invention features small nucleic acid molecules, such as short interfering nucleic acid (siNA), short interfering RNA (siRNA), double-stranded RNA (dsRNA), micro-RNA (miRNA), and short hairpin RNA (shRNA) molecules and methods used to modulate the expression of MLCK genes.

A siNA of the invention can be unmodified or chemically-modified. A siNA of the instant invention can be chemically synthesized, expressed from a vector or enzymatically synthesized. The instant invention also features various chemically-modified synthetic short interfering nucleic acid (siNA) molecules capable of modulating MLCK gene expression or activity in cells by RNA interference (RNAi). The use of chemically-modified siNA improves various properties of native siNA molecules through, for example, increased resistance to nuclease degradation in vivo and/or through improved cellular uptake. Furthermore, siNA having multiple chemical modifications may retain its RNAi activity. The siNA molecules of the instant invention provide useful reagents and methods for a variety of therapeutic, diagnostic, target validation, genomic discovery, genetic engineering, and pharmacogenomic applications.

FIGURES

FIG. 1. Knockdown of endogenous expression of MLCK-L with siRNA (A) After 48 hr, cells transfected with MLCK-L siRNA sequences (1-3) or control cells were lysed and Western blotted using MLCK antibody to detect protein expression. (B) Plot shows mean±SE of percent reduction in MLCK-L expression after knockdown normalized against MLCK-L expression in control cells. * indicates decrease in MLCK-L expression in seq3 siRNA transfected cells (p<0.05).

```
Sequence 1 corresponds to:
NNGGACUGCGCUGUUAUUGAG.        (SEQ ID NO: 1)

Sequence 2 corresponds to:
NNGUGGAAAGGCUUGCCGUGA.        (SEQ ID NO:2)

Sequence 3 corresponds to:
NNUGGGCAGCCCAUCCAGUAC.        (SEQ ID NO:3)
```

Figure 2:
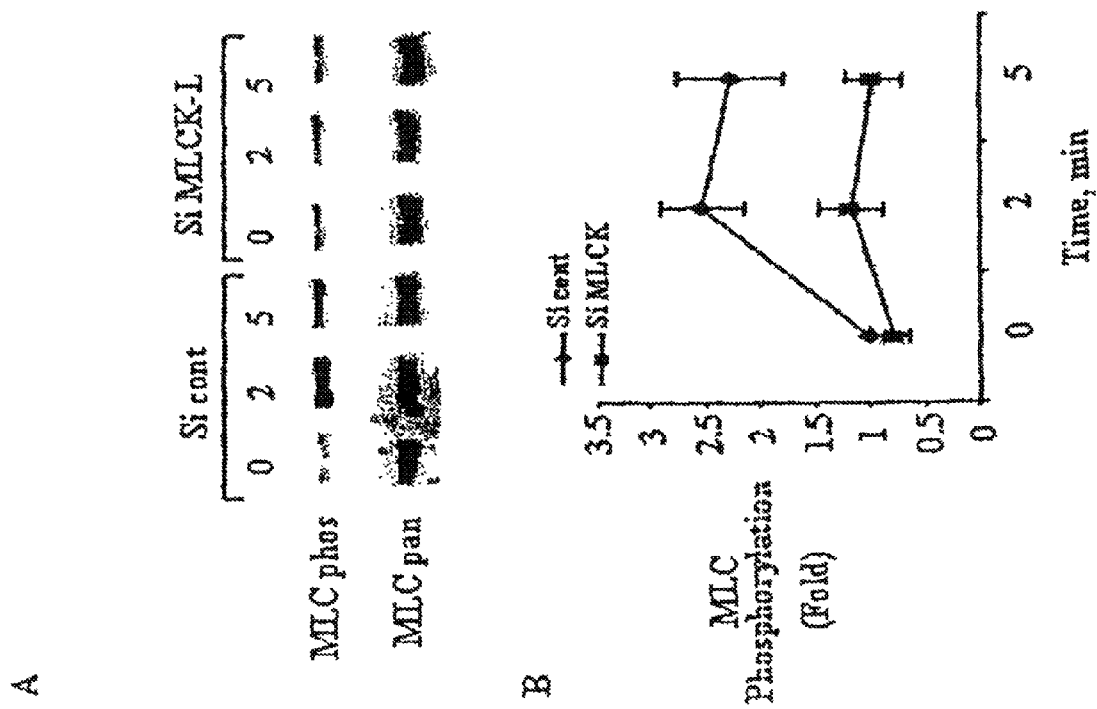

FIG. 2. Effect of MLCK-L knockdown on MLC phosphorylation in response to thrombin (A) Western blot showing MLC phosphorylation in response to thrombin in cells transfected with control (cont si) or MLCK-L (Si-MLCK-L) siRNA. Cells were stimulated with thrombin 48 hr post transfection and lysed. Lysates were Western blotted with phospho-MLC (top panel) or pan MLC Abs (bottom panel) to determine MLC phosphorylation. (B) Scatter plot showing mean±SEM of MLC phosphorylation normalized to total MLC in control or MLCK-L siRNA transfected monolayers (n=3).

Figure 3:
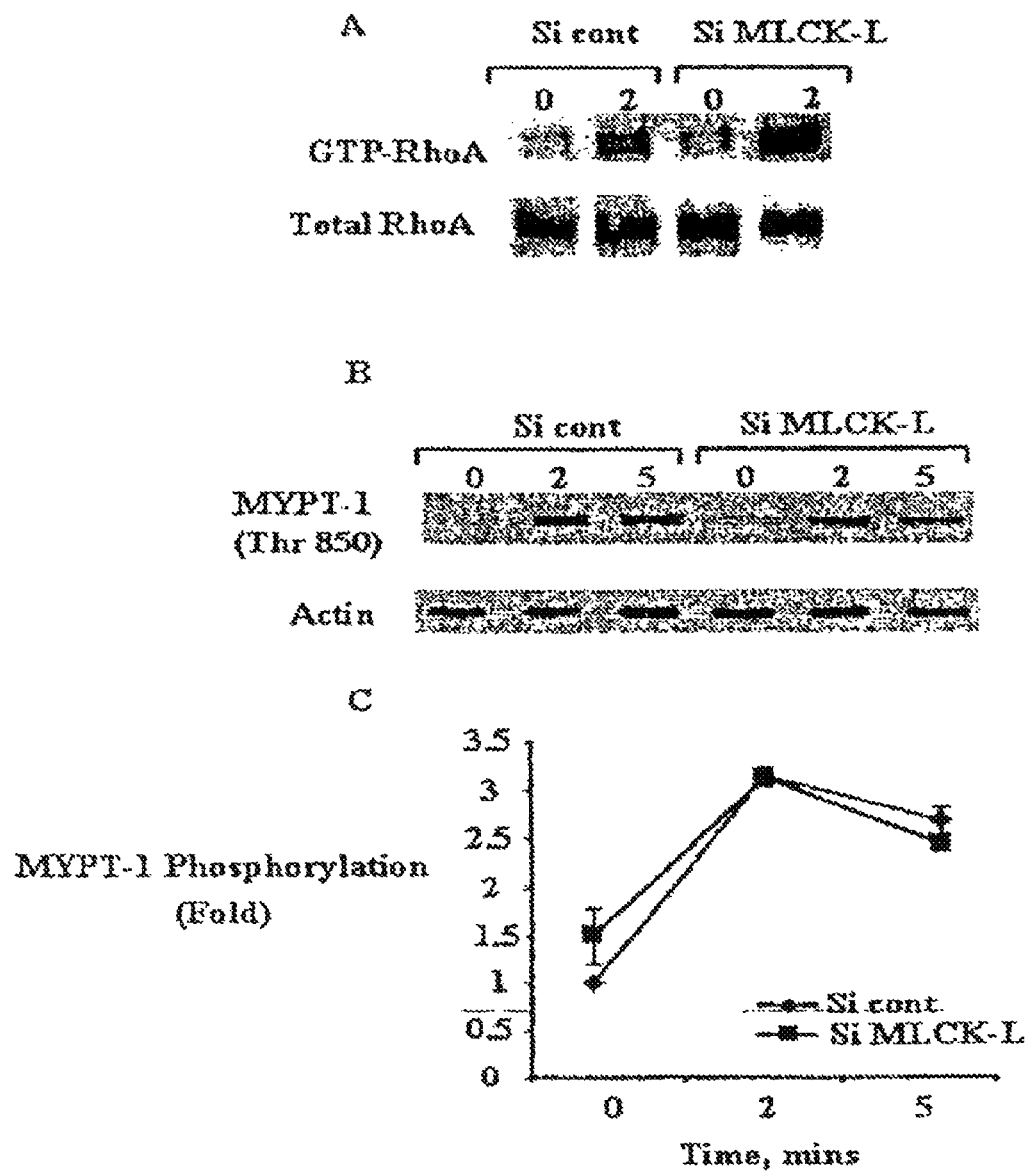

FIG. 3. Effect of MLCK-L knockdown on thrombin-induced RhoA signaling (A) RhoA activity after 2 min thrombin stimulation of control or MLCK-L siRNA transfected HPAE cells. RhoA activation is measured by the increased amount of GTP-bound RhoA (top) compared to total amount of RhoA in whole cell lysates (bottom). (B) MYPT phosphorylation induced by thrombin in control (cont Si) or MLCK-L (Si MLCK) siRNA transfected HPAE cells. Bottom panel shows equal protein loading as analyzed by Western blotting with actin Ab. (C), scatter plot showing mean±SEM of MYPT phosphorylation normalized to actin in control or MLCK-L siRNA transfected monolayers (n=3).

Figure 4:
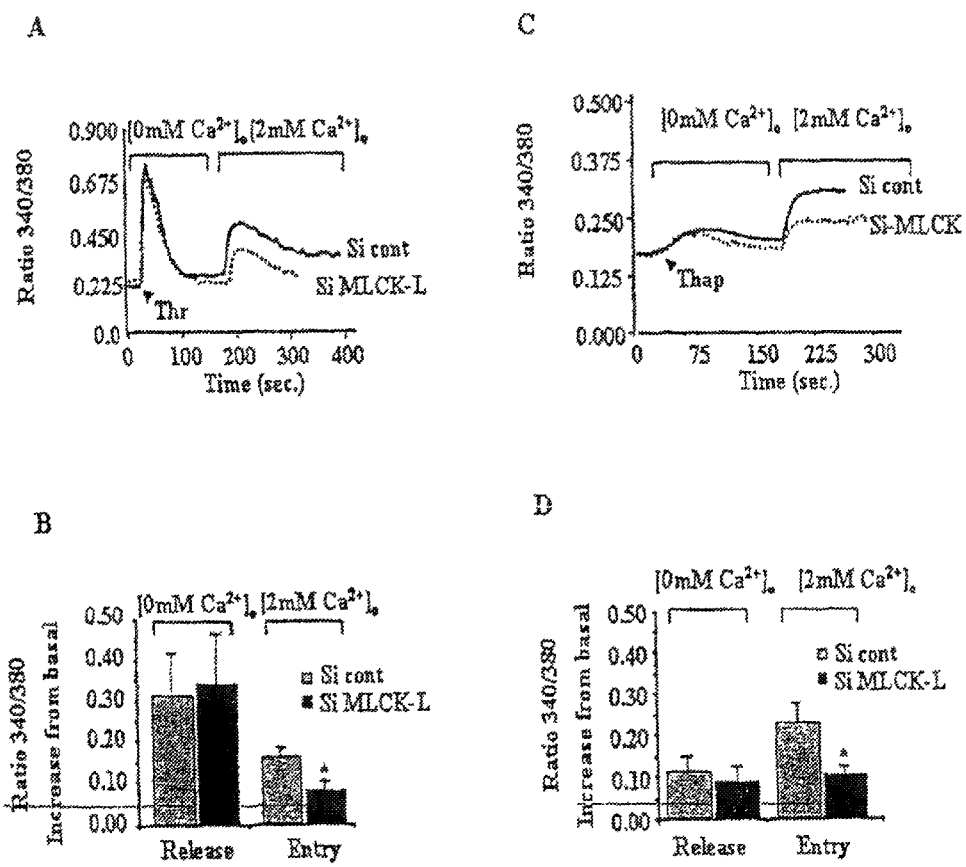

FIG. 4. Effect of MLCK-L knockdown on store operated calcium entry

Ratiometric measurements of $[Ca^{2+}]_i$ during extracellular $Ca^{2+}$ depletion-repletion conditions after depletion of stores with thrombin (A-B) or thapsigargin (C-D) in cells transfected with control (cont Si; solid line) or MLCK-L siRNA (Si MLCK; broken line). Measurements were made 48 hr post transfection after loading HPAE cell monolayer with Fura 2-AM for 15 min. Each representative tracing is the average response of 30-40 cells, and experiments were repeated three times. B and D, plot shows mean±SEM of $[Ca^{2+}]_i$ following store depletion or $Ca^{2+}$ entry in two groups (n=5). * indicates reduced $Ca^{2+}$ entry in MLCK-L knockdown cells compared to cells transfected with control siRNA transfected cells (P<0.05).

FIG. 5. MLCK-L knockdown effect on throbin stimulated aderens junction disassembly Cells transfected with control (Cont Si) or MLCK-L (Si MLCK-L) siRNA were stimulated with thrombin 48 hr post transfection and fixed followed by staining with VE-cadherin and Alexa-labeled secondary Ab to determine adherens junction dis-assembly by confocal imaging.

Figure 6:
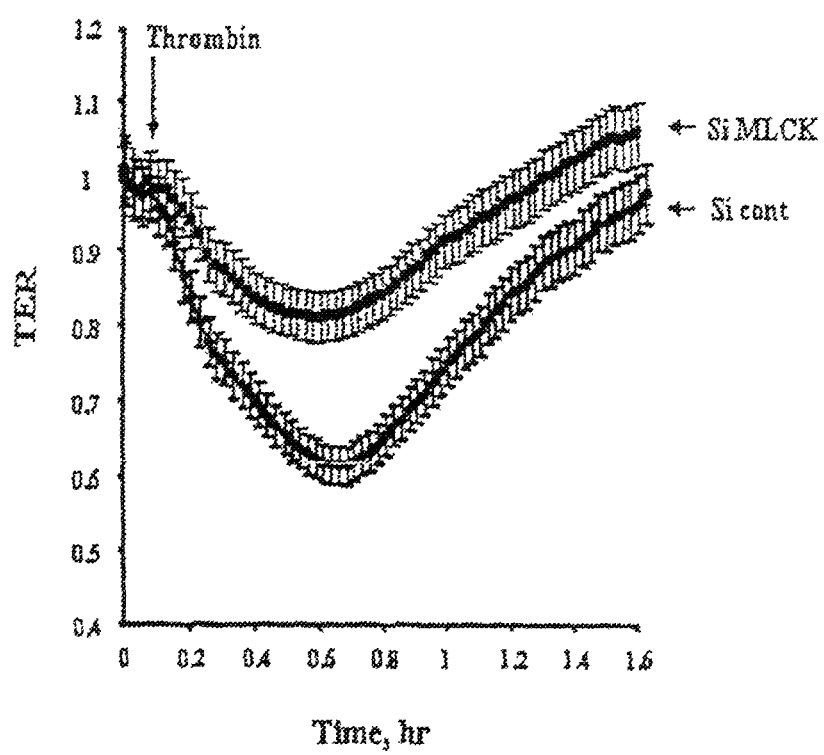

FIG. 6. MLCK-L knockdown effect on thrombin stimulated barrier dysfunction

Transendothelial electrical resistance (TER) measurements in HPAE cells transfected with control (cont Si) or MLCK-L (Si MLCK-L) siRNA. Data represent mean±SE from multiple experiments (n=5).

Figure 7:
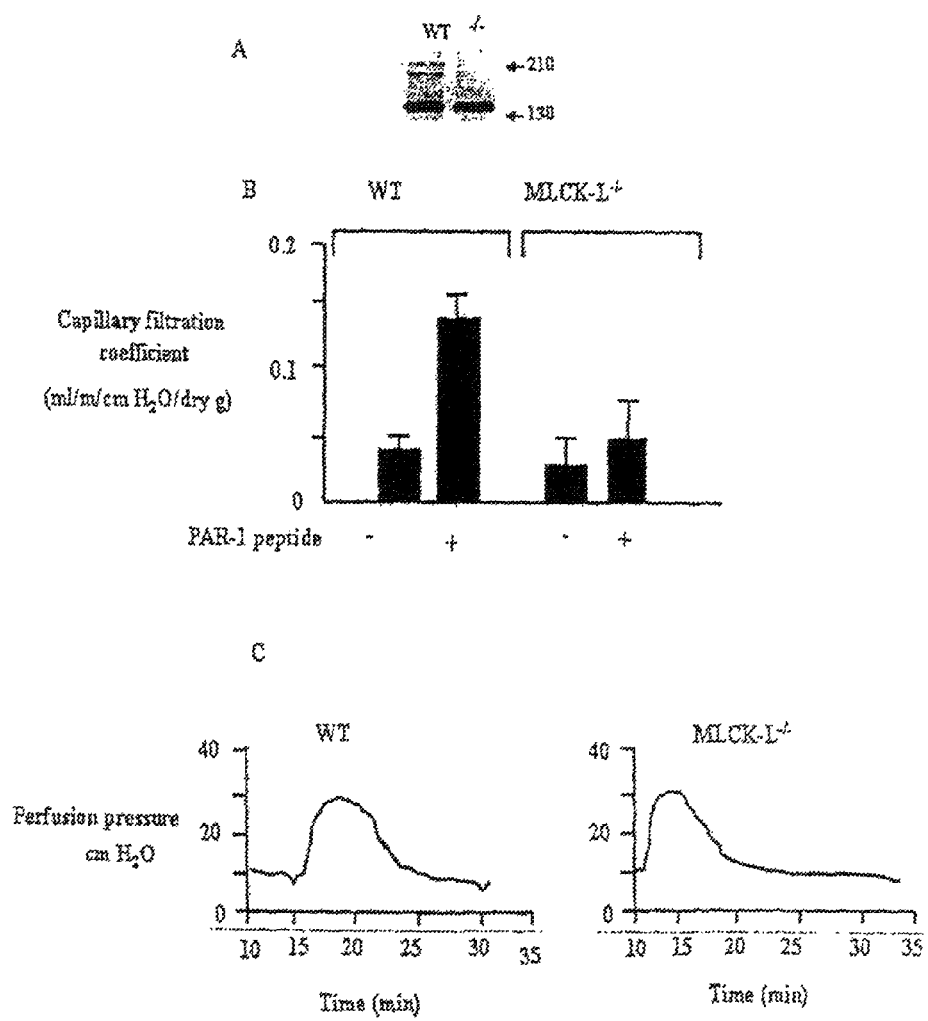

FIG. 7. Effects of PAR-1 agonist peptide on pulmonary microvessel liquid permeability ($K_{fc}$) in lungs isolated from Wt or MLCK-L knockout mice (A) Immunoblot of lung homogenate with MLCK antibody shows absence of MLCK-L 210 in MLCK$^{-/-}$ mice lungs but expression of 130 KD smooth muscle MLCK isoform is not affected. (B) After attaining isogravimetric conditions in the lungs, venous pressure was raised to 10 cm $H_2O$ to determine changes in $K_{fc}$. Results are mean±SE of 4 experiments. C, PAR-1 peptide induced vasoconstrictor response in lungs isolated from Wt or MLCK$^{-/-}$ mice.

Figure 8:
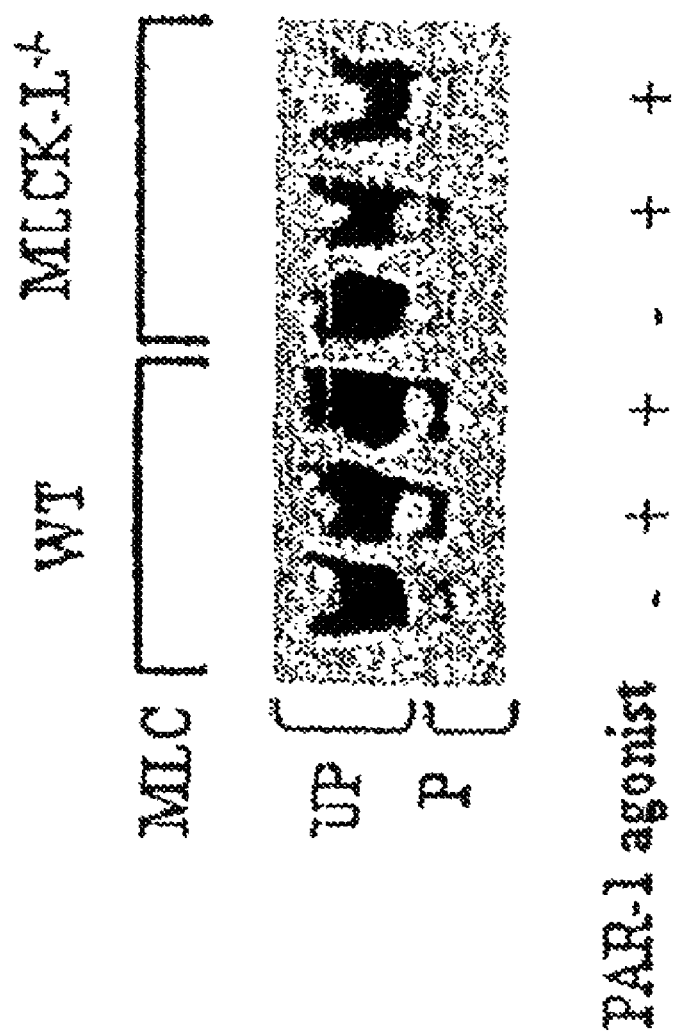

FIG. 8. Western blot showing unphosphorylated (UP) and phosphorylated foul) (P) of mouse lung myosin light chain (MLC)

WT (wild type) or MLCK-L$^{-/-}$ lung preparations were preperfused for 7 min with PAR-1 peptide and MLC phosphorylation was determined by Western blotting with anti-MLCK antibody following urea gel electrophoresis.

Figure 9:
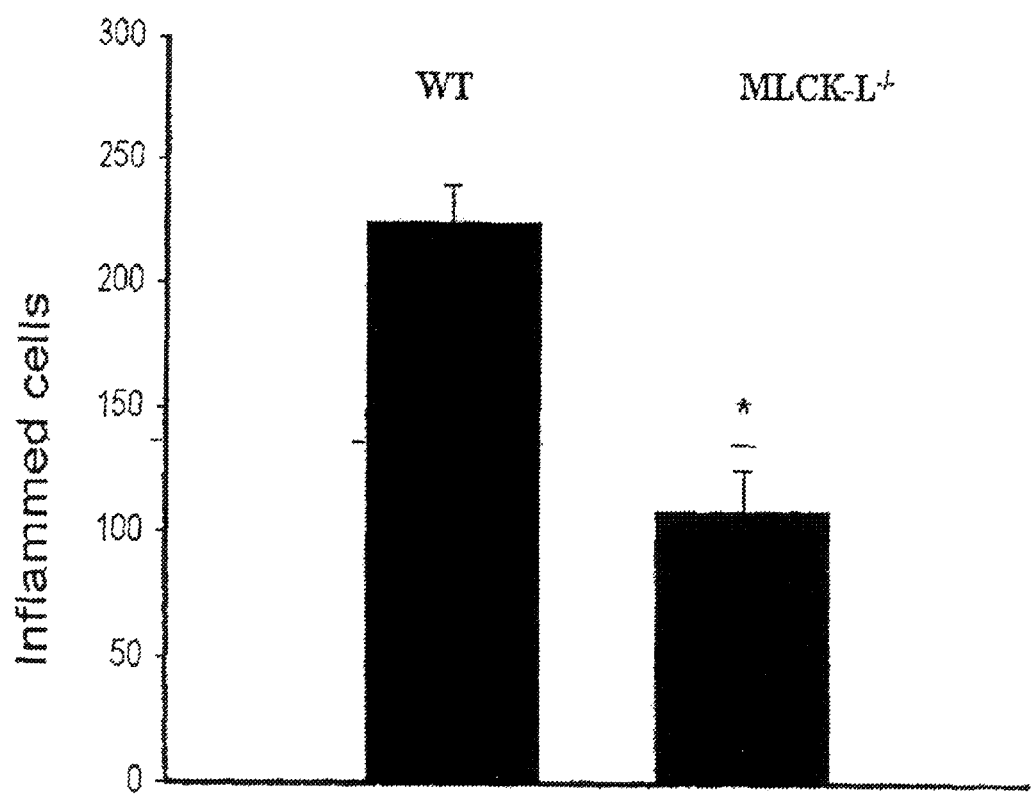

FIG. 9. Inhibition of eye inflammation in mouse model lacking the MLCK gene

Numbers of inflammatory cells in subconjunctival areas in paraffin eye sections were counted. The value was normalized to the number of inflammatory cells per unit area (2500 μm$^2$) underneath the conjunctival epithelium. For each treatment at least 4 mice were used.

Figure 10:
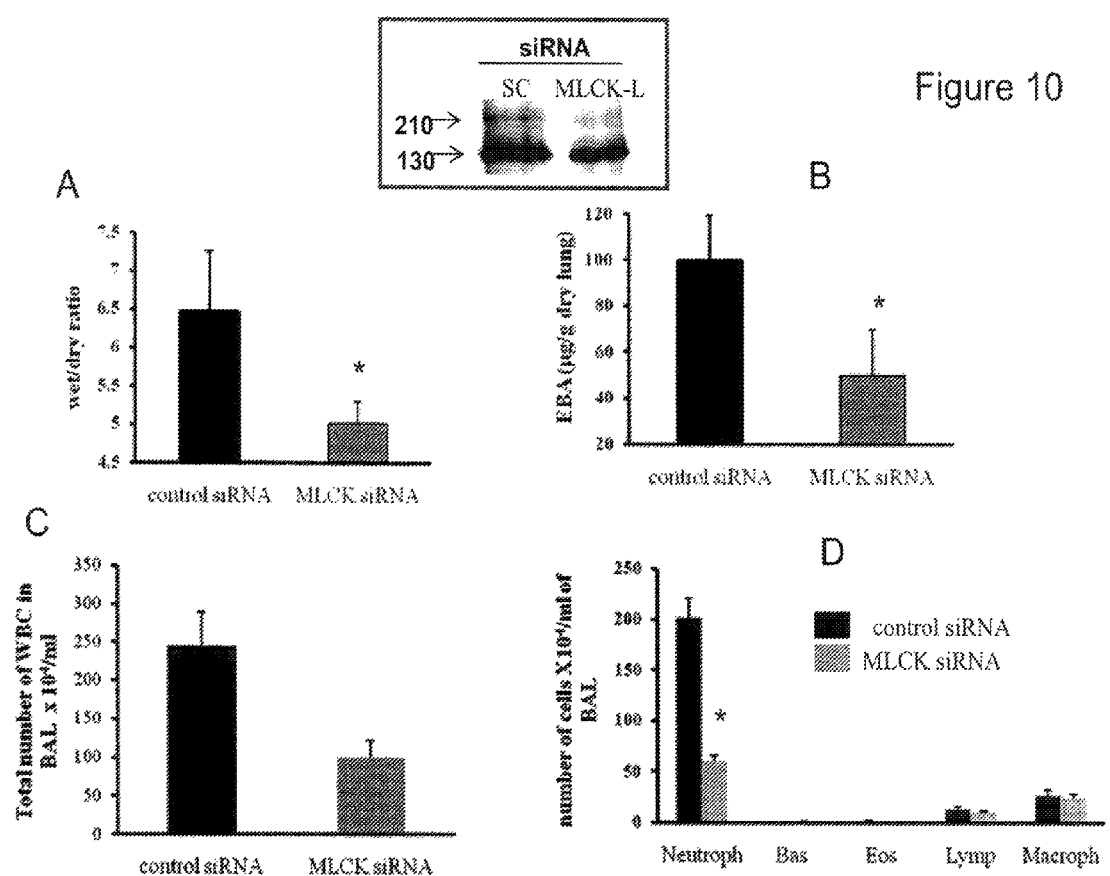

FIG. 10. MLCK-L siRNA prevents LPS-induced lung injury

After 48 hours mice (C56Bl/J) injected with scrambled (Sc) or MLCK-L siRNA were challenged with PBS or 1 mg/ml LPS through nebulizer for 45 min. Lungs were harvested after 4 hr of LPS challenge. Inset: Immunoblot of mouse lung injected with MLCK-L siRNA shows decrease in MLCK-L protein expression (210 kD). Note: MLCK-L siRNA had minimal effect on short (130 kD) smooth muscle MLCK isoform. (A) lung wet- dry-weight ratio in mice receiving Sc or MLCK-SiRNA. (B) albumin accumulation in mouse lungs receiving Sc or MLCK-SiRNA. Evans-blue tagged albumin was injected into vasculature of 30 min before terminating the experiment and accumulation of Evans-blue was determined. (C-D) Inflammatory cells accumulation in brochoalveolar lavage of mice receiving Sc or MLCK-SiRNA. Neutph, neutrophils; Bas, basophils; Eos, eosinophils; lymph, lymphocytes; macroph, macrophages.

DESCRIPTION

The present invention relates to compounds and methods which are useful in molecular investigations of MLCK, and, in the diagnosis, prevention, and therapy of tissue inflammation and angiogenesis. These compounds are stable nucleic acid agents which may be used to knockdown or down regulate MLCK-L. An example of one such nucleic acid agent is a siRNA as herein described.

Glossary

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described.

As used herein, particularly in the claims, the words "a" and "an" mean the same as the phrases "one and more than one" and "at least one" and explicitly are not limited to the singular, or to just one. For example, "a host cell" refers to at least one host cell and includes more than one host cell.

As used herein, particularly in the claims, the word "the" includes the plural as well as the singular and refers to "one or more than one" and "at least one." For example, "the siRNA" refers to at least one siRNA, and includes one and more than one siRNA.

The word "specifically" as used herein in, particularly as to the phrase "specifically cleaves MLCK-L RNA," means that at least 50% of all the RNAs that are cleaved are MLCK-L RNAs.

The term "substantially" as used herein, in particular in the phrase "substantially does not cleave" means cleavage does not occur or is inefficient. For instance, in a method of treatment the phase means that cleavage, to the extent it occurs at all, does not engender deleterious and/or adverse effects on a patient.

The term "more efficiently" as used herein means greater than.

The term "siRNA" refers to a small interfering RNA(s), which also has been referred to in the art as short interfering RNA and silencing RNA, among others. siRNAs generally are described as relatively short, often 20-25 nucleotide-long, double-stranded RNA molecules that are involved in RNA interference (RNAi) pathway(s). Generally, siRNAs are, in part, complementary to specific mRNAs and mediate their down regulation (hence, "interfering"). siRNAs thus can be used for down regulating the expression of specific genes and gene function in cells and organisms. siRNAs also play a role in related pathways. The general structure of most naturally occurring siRNAs is well established. Generally, siRNAs are short double-stranded RNAs, usually 21 nucleotides long, with two nucleotides single stranded "overhangs" on the 3 of each strand. Each strand has a 5' phosphate group and a 3' hydroxyl (—OH) group. In vivo, the structure results from processing by the enzyme "dicer," which enzymatically converts relatively long dsRNAs and relatively small hairpin RNAs into siRNAs.

The term siNA refers to a nucleic acid that acts like a siRNA, as described herein, but may be other than an RNA, such as a DNA, a hybrid RNA:DNA or the like. siNAs function like siRNAs to down regulate expression of gene products. See siRNA.

The term "RNA interference" which also has been called "RNA mediated interference" refers to the cellular processes by which RNA (such as siRNAs) down regulate expression of genes; i.e., down regulate or extinguish the expression of gene functions, such as the synthesis of a protein encoded by a gene. Typically, double-stranded ribonucleic acid inhibits the expression of genes with complementary nucleotide sequences. RNA interference pathways are conserved in most eukaryotic organisms. It is initiated by the enzyme dicer, which cleaves RNA, particularly double-stranded RNA, into short double-stranded fragments 20-25 base pairs long. One strand of the double-stranded RNA (called the "guide strand") is part of a complex of proteins called the RNA-induced silencing complex (RISC). The thus incorporated guide strand serves as a recognition sequence for binding of the RISC to nucleic acids with complementary sequences. Binding by RISC to complementary nucleic acids results in their being "silenced." The best studied silencing is the binding of RISCs to RNAs resulting in post-transcriptional gene silencing. Regardless of mechanism, interfering nucleic acids and RNA interference result in down regulation of the target gene or genes that are complementary (in pertinent part) to the guide strand.

A polynucleotide can be delivered to a cell to express an exogenous nucleotide sequence, to inhibit, eliminate, augment, or alter expression of an endogenous nucleotide sequence, or to affect a specific physiological characteristic not naturally associated with the cell. The polynucleotide can be a sequence whose presence or expression in a cell alters the expression or function of cellular genes or RNA. A delivered polynucleotide can stay within the cytoplasm or nucleus apart from the endogenous genetic material. Alternatively, DNA can recombine with (become apart of) the endogenous genetic material. Recombination can cause DNA to be inserted into chromosomal DNA by either homologous or non-homologous recombination.

A polynucleotide-based gene expression inhibitor comprises any polynucleotide containing a sequence whose presence or expression in a cell causes the degradation of or inhibits the function, transcription, or translation of a gene in a sequence-specific manner. Polynucleotide-based expression inhibitors may be selected from the group comprising: siRNA, microRNA, interfering RNA or RNAi, dsRNA, ribozymes, antisense polynucleotides, and DNA expression cassettes encoding siRNA, microRNA, dsRNA, ribozymes or antisense nucleic acids. SiRNA comprises a double stranded structure typically containing 15 to 50 base pairs and preferably 19 to 25 base pairs and having a nucleotide sequence identical or nearly identical to an expressed target gene or RNA within the cell. An siRNA may be composed of two annealed polynucleotides or a single polynucleotide that forms a hairpin structure. MicroRNAs (miRNAs) are small noncoding polynucleotides, about 22 nucleotides long, that direct destruction or translational repression of their mRNA targets. Antisense polynucleotides comprise a sequence that is complimentary to a gene or mRNA. Antisense polynucleotides include, but are not limited to: morpholinos, 2'-O-methyl polynucleotides, DNA, RNA and the like. The polynucleotide-based expression inhibitor may be polymerized in vitro, recombinant, contain chimeric sequences, or derivatives of these groups. The polynucleotide-based expression inhibitor may contain ribonucleotides, deoxyribonucleotides, synthetic nucleotides, or any suitable combination such that the target RNA and/or gene is inhibited.

Polynucleotides may contain an expression cassette coded to express a whole or partial protein, or RNA. An expression cassette refers to a natural or recombinantly produced polynucleotide that is capable of expressing a sequence. The cassette contains the coding region of the gene of interest along with any other sequences that affect expression of the sequence of interest. An expression cassette typically includes a promoter (allowing transcription initiation), and a transcribed sequence. Optionally, the expression cassette may include, but is not limited to, transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include, but is not limited to, translation termination signals, a polyadenosine sequence, internal ribosome entry sites (IRES), and non-coding sequences. The polynucleotide may contain sequences that do not serve a specific function in the target cell but are used in the generation of the polynucleotide.

Such sequences include, but are not limited to, sequences required for replication or selection of the polynucleotide in a host organism.

A polynucleotide can be delivered to a cell to study gene function. Delivery of a polynucleotide to a cell can also have potential clinical applications. Clinical applications include treatment of muscle disorders or injury, circulatory disorders, endocrine disorders, immune modulation and vaccination, and metabolic disorders (Baumgartner et al. 1998, Blau et al. 1995, Svensson et al. 1996, Baumgartner et al. 1998, Vale et al. 2001, Simovic et al. 2001).

A transfection agent, or transfection reagent, or delivery vehicle is a compound or compounds that bind(s) to or complex(es) with oligonucleotides and polynucleotides, and enhances their entry into cells. Examples of transfection reagents include, but are not limited to, cationic liposomes and lipids, polyamines, calcium phosphate precipitates, polycations, histone proteins, polyethylenimine, polylysine, and polyampholyte complexes. For delivery in vivo, complexes made with sub-neutralizing amounts of cationic transfection agent may be preferred. Non-viral vectors include protein and polymer complexes (polyplexes), lipids and liposomes (lipoplexes), combinations of polymers and lipids (lipopolyplexes), and multilayered and recharged particles. Transfection agents may also condense nucleic acids. Transfection agents may also be used to associate functional groups with a polynucleotide. Functional groups include cell targeting moieties, cell receptor ligands, nuclear localization signals, compounds that enhance release of contents from endosomes or other intracellular vesicles (such as membrane active compounds), and other compounds that alter the behavior or interactions of the compound or complex to which they are attached (interaction modifiers).

The term "naked nucleic acids" indicates that the nucleic acids are not associated with a transfection reagent or other delivery vehicle that is required for the nucleic acid to be delivered to a target cell.

"Inhibit" or "down-regulate" means that the expression of the gene, or level of RNAs or equivalent RNAs encoding one or more proteins or isoforms, or activity of one or more proteins, such as the MLCK-L or MLCK-S forms, is reduced below that observed in the absence of the nucleic acid molecules of the invention. In one embodiment, inhibition or down-regulation with the presently described nucleic acid molecules preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of MLCK with the nucleic acid molecule of the instant invention is greater in the presence of the nucleic acid molecule than in its absence.

By "up-regulate" is meant that the expression of the gene, or level of RNAs or equivalent RNAs encoding one or more proteins or isoforms, or activity of one or more proteins, such as MLCK-L or MLCK-S, is greater than that observed in the absence of the nucleic acid molecules of the invention. For example, the expression of a gene, such as the MLCK gene, can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more protein subunits, or activity of one or more proteins or protein isoforms is up-regulated or down-regulated, such that the expression, level, or activity is greater than or less than that observed in the absence of the nucleic acid molecules of the invention.

By "gene" it is meant a nucleic acid that encodes an RNA, for example, nucleic acid sequences including but not limited to structural genes encoding a polypeptide.

"Complementarity" refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, CSH Symp. Quant. Biol. LII pp. 123 (33; Frier et al., 1986, Proc. Nat. Acad. Sci. USA 83:9373 9377; Turner et al., 1987, J. Am. Chem. Soc. 109:3783 3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

By "RNA" is meant a molecule comprising at least one ribonucleotide residue. By "ribonucleotide" or "2'-OH" is meant a nucleotide with a hydroxyl group at the 2' position of a □-D-ribo-furanose moiety.

Nucleic Acid Modification.

Chemically synthesizing nucleic acid molecules with modifications (base, sugar and/or phosphate) that prevent their degradation by serum ribonucleases can increase their potency (see e.g., Eckstein et a)., International Publication No. WO 92/07065; Perrault et al., 1990 Nature 344, 565; Pieken et al., 1991, Science 253, 314; Usman and Cedergren, 1992, Trends in Biochem. Sci. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, TIBS. 17, 34; Usman et al., 1994, Nucleic Acids Symp. Ser. 31, 163; Burgin et al., 1996, Biochemistry, 35, 14090). Sugar modification of nucleic acid molecules have been extensively described in the art (see Eckstein et al., International Publication PCT No. WO 92/07065; Perrault et al. Nature, 1990, 344, 565 568; Pieken et al. Science, 1991, 253, 314 317; Usman and Cedergren, Trends in Biochem. Sci., 1992, 17, 334 339; Usman et al. International Publication PCT No. WO 93/15187; Sproat, U.S. Pat. No. 5,334,711 and Beigelman et al., 1995, J. Biol. Chem., 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, Tetrahedron Lett., 39, 1131; Earnshaw and Gait, 1998, Biopolymers (Nucleic acid Sciences), 48, 39 55; Velma and Eckstein, 1998, Annu. Rev. Biochem., 67, 99 134; and Burlina et al., 1997, Bioorg. Med. Chem., 5, 1999 2010; all of the references are hereby incorporated in their totality by reference herein). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Thus, in a cell and/or in vivo the activity can not be significantly lowered. Therapeutic nucleic acid molecules delivered exogenously are optimally stable within cells until translation of the target RNA has been inhibited long enough to reduce the levels of the undesirable protein. This period of time varies between hours to days depending upon the disease state. Nucleic acid molecules are preferably resistant to nucleases in order to function as effective intracellular therapeutic agents. Improvements in the chemical synthesis of RNA and DNA (Wincott et al., 1995 Nucleic Acids Res. 23, 2677; Caruthers et al., 1992, Methods in Enzymology 211,3 19 (incorporated by reference herein) have expanded the ability to modify nucleic acid molecules by introducing nucleotide modifications to enhance their nuclease stability as described above.

In one embodiment, the invention features a double-stranded short interfering nucleic acid (siNA) molecule that down-regulates expression of a MLCK gene, wherein the siNA molecule comprises about 19 to about 21 base pairs, and wherein each strand of the siNA molecule comprises one or more chemical modifications. In another embodiment, one of the strands of the double-stranded siNA molecule comprises a nucleotide sequence that is complementary to a nucleotide sequence of a MLCK gene or a portion thereof, and the second strand of the double-stranded siNA molecule comprises a nucleotide sequence substantially similar to the nucleotide sequence or a portion thereof of the targeted gene. In another embodiment, one of the strands of the double-stranded siNA molecule comprises a nucleotide sequence that is complementary to a nucleotide sequence of a MLCK gene or a portion thereof, and the second strand of the double-stranded siNA molecule comprises a nucleotide sequence substantially similar to the nucleotide sequence or a portion thereof of the MLCK gene. In another embodiment, each strand of the siNA molecule comprises about 19 to about 23 nucleotides, and each strand comprises at least about 19 nucleotides that are complementary to the nucleotides of the other strand. The MLCK gene may comprise, for example, the sequence referred to in Table I, or a sub-sequence thereof.

In embodiment of the invention the siNA comprises a sequence that has greater complementarity to MLCK-L than MLCK-S and directs down regulation of MLCK-L more efficiently than it directs down regulation of MLCK-S. In embodiments in this regard the siNA contains a region that is at least 90% identical in sequence to a region of MLCK-L inRNA but is less than 50% identical to any region in MLCK-S inRNA. In embodiments the siRNA comprises a region having a sequence comprised within the MLCK-L sequence from nucleotides 1428 to 1638 (inclusive) in SEQ/ ID NO 24 (or its complement). In embodiments said sequence in MLCK-L is not found in MLCK-S.

TABLE I

```
Homo sapiens myosin light chain                                                        (SEQ ID NO: 4)
polypeptide kinase isoform 1        1 ccatgggga tgtgaagctg gttgcctcgt cacacatttc caaaacctcc ctcagtgtgg
(MLCK)                             61 atccctcaag agttgactcc atgcccctga cagaggcccc tgctttcatt ttgcccctc
Accession: AY424270               121 ggaacctctg catcaaagaa ggagccaccg ccaagttcga agggcgggtc cggggttacc
5776 bp mRNA linear Complete      181 cagagcccca ggtgacatgg cacagaaacg ggcaacccat caccagcggg ggccgcttcc
CDS; alternatively spliced        241 tgctggattg cggcatccgg gggacttta gccttgtgat tcatgctgtc catgaggagg
                                  301 acaggggaaa gtatacctgt gaagccacca atgcagtgg tgctcgccag gtgacagtgg
                                  361 agttgacagt agaaggaagt tttgcgaagc agcttggtca gcctgttgtt tccaaaacct
                                  421 taggggatag attttcagct tcagcagtgg agacccgtcc tagcatctgg ggggagtgcc
                                  481 caccaaagtt tgctaccaag ctgggccgag ttgtggtcaa agaaggacag atgggacgat
                                  541 tctcctgcaa gatcactggc cggcccaac cgcaggtcac ctggctcaag ggaaatgttc
                                  601 cactgcagcc gagtgcccgt gtgtctgtgt ctgagaagaa cggcatgcag gttctggaaa
                                  661 tccatggagt caaccaagat gacgtgggag tgtacacgtg cctggtggtg aacgggtcgg
                                  721 ggaaggcctc gatgtcagct gaactttcca tccaaggttt ggacagtgcc aataggtcat
                                  781 ttgtgagaga aacaaaagcc accaattcag atgtcaggaa agaggtgacc aatgtaatct
                                  841 caaaggagtc gaagctggac agtcttggagg ctgcagccaa aagcaagaac tgctccagcc
                                  901 cccagagagg tggctcccca ccctgggctg caaacagcca gcctcagccc caagggagt
                                  961 ccaagctgga gtcatgcaag gactcgccca gaacggcccc gcagacccg gtccttcaga
                                 1021 agacttccag ctccatcacc ctgcaggccg caagagttca gccggaacca agagcaccag
                                 1081 gcctggggt cctatcacct tctggagaag agaggaagag gccagctcct ccccgtccag
                                 1141 ccaccttccc caccaggcag cctggcctgg ggagccaaga tgttgtgagc aaggctgcta
                                 1201 acaggagaat cccatggag ggccagaggg attcagcatt ccccaaattt gagagcaagc
                                 1261 cccaaagcca ggaggtcaag gaaaatcaaa ctgtcaagtt cagatgtgaa gtttccggga
                                 1321 ttccaaagcc tgaagtggcc tggttcctgg aaggcacccc cgtgaggaga caggaaggca
                                 1381 gcattgaggt ttatgaaaat gctggctccc attacctctg cctgctgaaa gcccggacca
                                 1441 gggacagtgg gacatacagc tgcactgctt ccaacgccca aggccaggtg tcctgtagct
                                 1501 ggaccctcca agtggaaagg cttgccgtga tggaggtggc ccctccttc tccagtgtcc
```

TABLE I-continued

```
1561 tgaaggactg cgctgttatt gagggccagg attttgtgct gcagtgctcc gtacggggga
1621 ccccagtgcc ccggatcact tggctgctga atgggcagcc catccagtac gctcgctcca
1681 cctgcgaggc cggcgtggct gagctccaca tccaggatgc cctgccggag gaccatggca
1741 cctacacctg cctagctgag aatgccttgg ggcaggtgtc ctgcagcgcc tgggtcaccg
1801 tccatgaaaa gaagagtagc aggaagagtg agtaccttct gcctgtggct cccagcaagc
1861 ccactgcacc catcttcctg cagggcctct ctgatctcaa agtcatggat ggaagccagg
1921 tcactatgac tgtccaagtg tcagggaatc caccccctga agtcatctgg ctgcacaatg
1981 ggaatgagat ccaagagtca gaggacttcc actttgaaca gagaggaact cagcacagcc
2041 tttgtatcca ggaagtgttc ccggaggaca cgggcacgta cacctgcgag gcctggaaca
2101 gcgctggaga ggtccgcacc caggccgtgc tcacggtaca agagcctcac gatggcaccc
2161 agccctggtt catcagtaag cctcgctcag tgacagcctc cctgggccag agtgtcctca
2221 tctcctgcgc catagctggt gacccctttc ctaccgtgca ctggctcaga gatggcaaag
2281 ccctctgcaa agacactggc cacttcgagg tgcttcagaa tgaggacgtg ttcaccctgg
2341 ttctaaagaa ggtgcagccc tggcatgccg gccagtatga gatcctgctc aagaaccggg
2401 ttggcgaatg cagttgccag gtgtcactga tgctacagaa cagctctgcc agagccttc
2461 cacgggggag ggagcctgcc agctgcgagg acctctgtgg tggaggagtt ggtgctgatg
2521 gtggtggtag tgaccgctat gggtccctga ggcctggctg gccagcaaga gggcagggtt
2581 ggctagagga ggaagacggc gaggacgtgc gaggggtgct gaagaggcgc gtggagacga
2641 ggcagcacac tgaggaggcg atccgccagc aggaggtgga gcagctggac ttccgagacc
2701 tcctggggaa gaaggtgagt acaaagaccc tatcggaaga cgacctgaag gagatcccag
2761 ccgagcagat ggatttccgt gccaacctgc aacggcaagt gaagccaaag actgtgtctg
2821 aggaagagag gaaggtgcac agcccccagc aggtcgattt tcgctctgtc ctggccaaga
2881 aggggacttc caagaccccc gtgcctgaga aggtgccacc gccaaaacct gccaccccgg
2941 attttcgctc agtgctgggt ggcaagaaga aattaccagc agagaatggc agcagcagtg
3001 ccgagaccct gaatgccaag gcagtggaga gttccaagcc cctgagcaat gcacagcctt
3061 cagggcccct gaaacccgtg ggcaacgcca agcctgctga gaccctgaag ccaatgggca
3121 acgccaagcc tgccgagacc ctgaagccca tgggcaatgc caagcctgat gagaacctga
3181 aatccgctag caaagaagaa ctcaagaaag acgttaagaa tgatgtgaac tgcaagagag
3241 gccatgcagg gaccacagat aatgaaaaga gatcagagag ccaggggaca gccccagcct
3301 tcaagcagaa gctgcaagat gttcatgtgg cagagggcaa gaagctgctg ctccagtgcc
3361 aggtgtcttc tgacccccca gccaccatca tctggacgct gaacggaaag accctcaaga
3421 ccaccaagtt catcatcctc tcccaggaag gctcactctg ctccgtctcc atcgagaagg
3481 cactgcctga ggacagaggc ttatacaagt gtgtagccaa gaatgacgct ggccaggcgg
3541 agtgctcctg ccaagtcact gtggatgatg ctccagccag tgagaacacc aaggcccag
3601 agatgaaatc ccggaggccc aagagctctc ttcctcccgt gctaggaact gagagtgatg
3661 cgactgtgaa aaagaaacct gcccccaaga cacctccgaa ggcagcaatg cccctcaga
3721 tcatccagtt ccctgaggac cagaaggtac gcgcaggaga gtcagtggag ctgtttggca
3781 aagtgacagg cactcagccc atcacctgta cctggatgaa gttccgaaag cagatccagg
3841 aaagcgagca catgaaggtg gagaacagcg agaatggcag caagctcacc atcctggccg
3901 cgcgccagga gcactgcggc tgctacacac tgctggtgga gaacaagctg ggcagcaggc
3961 aggcccaggt caacctcact gtcgtggata agccagaccc cccagctggc acaccttgtg
4021 cctctgacat tcggagctcc tcactgaccc tgtcctggta tggctcctca tatgatgggg
4081 gcagtgctgt acagtcctac agcatcgaga tctgggactc agccaacaag acgtggaagg
4141 aactagccac atgccgcagc acctctttca acgtccagga cctgctgcct gaccacgaat
4201 ataagttccg tgtacgtgca atcaacgtgt atggaaccag tgagccaagc caggagtctg
4261 aactcacaac ggtaggagag aaacctgaag agccgaagga tgaagtggag gtgtcagatg
4321 atgatgagaa ggagcccgag gttgattacc ggacagtgac aatcaatact gaacaaaaag
4381 tatctgactt ctacgacatt gaggagagat taggatctgg gaaatttgga caggtctttc
4441 gacttgtaga aaagaaaact cgaaagtct gggcagggaa gttcttcaag gcatattcag
4501 caaaagagaa agaaatatc cggcaggaga ttagcatcat gaactgcctc caccccccta
4561 agctggtcca gtgtgtggat gcctttgaag aaaaggccaa catcgtcatg gtcctggaga
4621 tcgtgtcagg aggggagctg tttgagcgca tcattgacga ggactttgag ctgacggagc
4681 gtgagtgcat caagtacatg cggcagatct cggagggagt ggagtacatc cacaagcagg
```

Use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of subjects with nucleic acid molecules can also include combinations of different types of nucleic acid molecules.

Therapeutic nucleic acid molecules (e.g., enzymatic nucleic acid molecules and antisense nucleic acid molecules) delivered exogenously are optimally stable within cells until translation of the target RNA has been inhibited long enough to reduce the levels of the undesirable protein. This period of time varies between hours to days depending upon the disease state. These nucleic acid molecules should be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In one embodiment, nucleic acid catalysts having chemical modifications that maintain or enhance enzymatic activity are provided. Such nucleic acids are also generally more resistant to nucleases than unmodified nucleic acid. Thus, in a cell and/or in vivo the activity of the nucleic acid cannot be significantly lowered. As exemplified herein such enzymatic nucleic acids are useful in a cell and/or in vivo even if activity over all is reduced about 10 fold (Burgin et al., 1996, Biochemistry, 35, 14090). Such enzymatic nucleic acids herein are said to "maintain" the enzymatic activity of an all RNA ribozyme or all DNA DNAzyme.

In another aspect of the invention, vectors, preferably expression vectors, contain nucleic acids encoding one or more siNAs, for example, miRNAs. As used herein, the term "vector" refers to a nucleic acid molecule capable of transporting another nucleic acid to which it has been linked. One type of a vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors. Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form plasmids. In the present specification, "plasmid" and "vector" can be used interchangeably as the plasmid is the most commonly used from of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers, and other expression control elements (e.g., polyadenylation signals). Such regulatory sequences are described, for example, in Goeddel; Gene Expression Technology: Methods in Enzymology 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein or RNA desired, etc. The expression vectors of the invention can be introduced into host cells to thereby produce siNAs, RNAs, proteins or peptides, including fusion proteins or peptides.

In another embodiment, a nucleic acid of the invention is expressed in mammalian cells using a mammalian expression vector. The recombinant mammalian expression vector may be capable of directing expression of the nucleic acid preferentially in a particular cell type (e.g., tissue-specific regulatory elements are used to express the nucleic acid). Tissue specific regulatory elements are known in the art. Non-limiting examples of suitable tissue-specific promoters include the albumin promoter, lymphoid-specific promoters, neuron specific promoters, pancreas specific promoters, and mammary gland specific promoters. Developmentally-regulated promoters are also encompassed, for example the murine box promoters and the □-fetoprotein promoter.

In another aspect the nucleic acid molecules comprise a 5' and/or a 3'-cap structure. By "cap structure" is meant chemical modifications, which have been incorporated at either terminus of the oligonucleotide (see, for example, Wincott et al, WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminis. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT Publication No. WO 97/26270, incorporated by reference herein).

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non-bridging methylphosphonate and 5'-mercapto moieties (for more details see Beaucage and Iyer, 1993, Tetrahedron 49, 1925; incorporated by reference herein).

The administration of the herein described nucleic acid molecules to a patient can be intravenous, intraarterial, intraperitoneal, intramuscular, subcutaneous, intrapleural, intrathecal, by perfusion through a regional catheter, or by direct intralesional injection. When administering these nucleic acid molecules by injection, the administration may be by continuous infusion, or by single or multiple boluses. The dosage of the administered nucleic acid molecule will vary depending upon such factors as the patient's age, weight, sex, general medical condition, and previous medical history. Typically, it is desirable to provide the recipient with a dosage of the molecule which is in the range of from about 1 pg/kg to 10 mg/kg (amount of agent/body weight of patient), although a lower or higher dosage may also be administered.

A composition is said to be a "pharmaceutically acceptable carrier" if its administration can be tolerated by a recipient patient. Sterile phosphate-buffered saline is one example of a pharmaceutically acceptable carrier. Other suitable carriers are well-known in the art. See, for example, REMINGTON'S PHARMACEUTICAL SCIENCES, 18$^{th}$ Ed. (1990).

For purposes of immunotherapy, an immunoconjugate and a pharmaceutically acceptable carrier are administered to a patient in a therapeutically effective amount. A combination of an immunoconjugate and a pharmaceutically acceptable carrier is said to be administered in a "therapeutically effective amount" if the amount administered is physiologically significant. An agent is physiologically significant if its presence results in a detectable change in the physiology of a recipient patient.

Additional pharmaceutical methods may be employed to control the duration of action of an immunoconjugate in a therapeutic application. Control release preparations can be prepared through the use of polymers to complex or adsorb an immunoconjugate. For example, biocompatible polymers include matrices of poly(ethylene-co-vinyl acetate) and matrices of a polyanhydride copolymer of a stearic acid dimer and sebacic acid. Sherwood et al., *Bio/Technology* 10:1446-1449 (1992). The rate of release of nucleic acid molecules from such a matrix depends upon the molecular weight of the molecule, the amount of molecule within the matrix, and the size of dispersed particles. Saltzman et al., Biophysical. J. 55:163-171 (1989); and Sherwood et al., *Bio/Technology* 10:1446-1449 (1992). Other solid dosage forms are described in REMINGTON'S PHARMACEUTICAL SCIENCES, 18th Ed. (1990).

Reducing or Eliminating MLCK-L Expression

The data presented herein establishes the role of the long MLCK isoform in regulating endothelial permeability in the intact microcirculation in response to permeability-increasing mediators. This has been shown using a recently developed strain of mice lacking the long isoform of MLCK (MLCK210$^{-/-}$ mice) and RNA silencing to reduce expression of MLCK-L in human endothelial cells. The findings demonstrate that thrombin-induced increase in lung microvessel permeability is prevented in MLCK-L$^{-/-}$ mice. In addition, using siRNA which specifically knockdown MLCK-L in human endothelial cells, the results show that MLCK-L suppresses the increase in intracellular $Ca^{2+}$ level induced by thrombin or thapsigargin by impairing SOC activity. The results identify MLCK-L as a key effector mediating the increase in vascular permeability by regulating the phosphorylation of MLC. We uncovered a novel role of MLCK in the apparently direct activation of SOCs leading to an MLCK-mediated enhancement of calcium entry.

Ultrastructural findings in the lung endothelium and extensive cell culture models have established that cell contraction leading to gap formation between endothelial cells is a primary determinant of increased endothelial permeability in response to agonists such as thrombin, histamine, and VEGF.[1] It is known that activation of the PAR-1 receptor by thrombin within seconds leads to a rise in intracellular $Ca^{2+}$ which is an essential signal inducing activation of the $Ca^{2+}$/CaM-dependent MLCK. MLCK causes actinomyosin stress fibers to develop force.[1] Further, studies showed that thrombin within minutes also activates the small GTPase RhoA which induces endothelial contraction. A general and well accepted model of RhoA regulation of endothelial contraction is that RhoA through its downstream effector, Rho kinase, can increase MLC phosphorylation by phosphorylation-mediated inhibition of myosin light chain phosphatase activity. Thus, intracellular $Ca^{2+}$ rise, MLCK and RhoA activation, and endothelial contraction all precede the formation of interendothelial gaps.[1] Studies using pharmacologic as well as constitutively active recombinant MLCK protein established that MLCK by phosphorylating MLC is intimately involved in regulating endothelial permeability in cultured monolayers or in in vivo models of vascular permeability regulation.[4,5,3,6-10] Likewise, inhibition of both RhoA and Rho-kinase has also been shown to prevent the increase in endothelial permeability.[1] Thus, the question whether RhoA, MLCK, or the calcium ion plays the dominant role in controlling MLC phosphorylation in endothelial cells in response to permeability-increasing mediators is unresolved. In this regard, we showed that suppression of endogenous MLCK-L in human endothelial cells prevented MLC phosphorylation in the presence of normal RhoA as well as Rho kinase activities. Thus our results support the concept that MLCK-L activity is required for MLC phosphorylation to occur and the Rho-ROCK pathway may be able to sustain this response.

Studies show that $Ca^{2+}$ entry via store-operated cation (SOC) channels plays a crucial role in sustaining the increase in intracellular $Ca^{2+}$ following depletion of endoplasmic reticulum (ER) stores.[22, 25-30] We found that knock-down of MLCK-L significantly inhibited SOC induced $Ca^{2+}$ entry either induced by thrombin or thapsigargin. These findings support previous studies in which pharmacologic inhibition of MLCK was shown to suppress SOC-mediated $Ca^{2+}$ entry in endothelial cells.[31] MLCK-L could regulate the SOC activation either by phosphorylating the SOC channels or by maintaining their surface expression.[1, 32] Findings from our group as well as others have implicated the transient receptor potential canonical (TRPC) channels constitute SOC in endothelial cells.[1] Additional studies will be required to identify the target of MLCK-L.

Since MLCK-L was required for MLC phosphorylation as well as SOC activation, we addressed the role of MLCK-L in mediating the increase in endothelial permeability in cultured cells as well as intact microcirculation. An important clue that MLCK-L plays an important role in regulating lung injury was recently provided by Wainwright et al[6] who developed a strain of mice in which the long isoform of MLCK was deleted (MLC-LK$^{-/-}$). They demonstrated that in contrast to WT mice i.p. injection of the bacterial product LPS produced significantly less damage in the lungs of MLCK-L$^{-/-}$ mice as reflected by interstitial hemorrhage, inflammatory cell infiltrate, and atelectasis.[6] Furthermore, deletion of MLCK-L in mice enhanced survival during subsequent mechanical ventilation. Because in addition to endothelium, MLCK-L may be expressed in other non-muscle cells such as neutrophils and macrophages, it is possible that the protective effect of MLCK-L observed in this study could have been due to the altered function of inflammatory cells. Using an isolated perfused lung model, we showed that PAR-1 activation did not elicite increased lung microvessel permeability in MLCK-L$^{-/-}$ mice. In addition, we observed that PAR-1-induced MLC phosphorylation was decreased in lung tissue taken from MLCK-L null mice. We also showed essentially normal PAR-1-induced pulmonary vasoconstriction in. MLCK-L deficient mice indicating that a smooth muscle isoform was functioning in intact lungs as expected. A recent study similarly found that the MLCK-L deletion did not alter the contractility response of isolated aortic rings to vasoconstrictor or vasodilator agonists.[33] Thus, the results of the present study identify the specific role of MLCK-L in the mechanism of endothelial permeability increase in contrast to the short isoform specific to vascular smooth muscle cells, which mediates vasoconstriction. We also demonstrated using TER measurement that MLCK-L plays an essential role in regulating endothelial barrier function because knock-down of MLCK-L inhibited TER response in PAR-1.

The data herein show that MLCK-L by inducing an increase in MLC phosphorylation and by augmenting the influx of $Ca^{2+}$ through the SOC channel is a key regulator of lung endothelial permeability.

Treatment of Endothelial Cells Dysfunctions and Diseases Thereof Such as Asthma, Adult Respiratory Stress Syndrome, Sepsis and Trauma The vascular endothelium lining the intima of blood vessels dynamically regulates a variety of cellular functions including vascular smooth muscle tone, host-defense reactions, wound healing, angiogenesis, and also provides a semi-selective barrier for tissue fluid hemostasis. Dysregulation of endothelial function leads to profound leakage of fluid and macromolecules into the lung tissue and airspace, resulting in tissue inflammation, a hall mark of Adult Respiratory Distress Syndrome (ARDS), sepsis and trauma. MLCK by monophosphorylating the regulatory MLC on Ser19 or by di-phosphorylating Ser19/Thr18 activates cell contraction which plays an important role in regulating several endothelial cell functions such as transendothelial PMN migration elicited by chemotactic agents and cell survival. Several studies using either constitutively active MLCK or pharmacological inhibitors of MLCK have shown that MLCK-induced MLC phosphorylation plays an essential role in regulating endothelial permeability in vitro and in vivo. Interestingly, endothelial cells and other inflammatory cells have been shown to predominantly express the long isoform of MLCK-L. Small nucleotide profiling of ARDS and asthma patients has identified MLCK-L to be pathogenic. Results using the mouse model, as described above, show that siMLCK-L inhibits endotoxin-induced loss of lung vascular function and, accordingly, indicates effectiveness of MLCK-L siRNA for clinical applications (treatment) of disorders and diseases involving endothelial cell dysfunction such as, but not limited to ARDS, sepsis, trauma, and asthma.

The invention is further illustrated by way of the following illustrative examples. However, it is to appreciated that the invention is not limited to the particular methodologies, protocols, reagents, results or the like described above and/or set forth in the illustrative examples. To the contrary, those of skill in the pertinent arts will readily ascertain from reading the present disclosure a wide variety of other specific embodiments of the invention that they can realize without undue experimentation. A full understanding of the invention and of the claimed subject matter set forth below may be had only by reading the present disclosure in full in light of the knowledge and insight of a person skilled in the arts pertinent thereto.

EXAMPLES

Example 1

Materials and Protocols for Assessing Microvessel Permeability in the Mouse Lung Human α-thrombin was obtained from Enzyme Research Laboratories (South Bend, Ind.). Human pulmonary arterial endothelial (HPAE) cells and endothelial growth medium (EBM-2) were obtained from Clonetics (San Diego, Calif.). Fura 2-AM, BAPTA-AM and fluorescent antibodies were purchased from Molecular Probes. Thapsigargin was obtained from Calbiochem (La Jolla, Calif.). Electrodes for endothelial monolayer electrical resistance measurements were obtained from Applied Biophysics (Troy, N.Y.). MLCK-L siRNA were custom synthesized by Dharmacon (Lafayette, Colo.). Anti-RhoA, anti-VE-cadherin antibodies and transfection reagents for siRNA were purchased from Santa Cruz Biotechnology (San Diego, Calif.), phospho-Thr850MYPT1 antibody was purchased from Upstate (Lake Placid, N.Y.) and anti-MLCK Clone K36 was purchased from Sigma (St Louis, Mo.). Rho activity was determined using GST-rhotekin-Rho-binding domain beads from Cytoskeleton (Denver, Colo.). Anti-phosho-MLC antibody was a gift from Dr. Jerold Turner (University of Chicago).

Endothelial Cell Culture

HPAE cells were cultured in T-75 flasks coated with 0.1% gelatin in EBM-2 medium supplemented with 10% FBS. In all experiments, HPAE cells between passage 6 and 8 were used.

Microvessel Permeability Studies in Mouse Lung

We measured microvessel permeability in the wild type and MLCK210$^{-/-}$ mice lung by determining microvascular filtration coefficient ($k_{f,c}$) as described.[20] Briefly, according to an approved protocol of the University of Illinois at Chicago Animal Care Committee, male mice weighing 25-30 g were anesthetized with a combination of 10 mg/ml ketamine, 0.25 mg/ml xylazine, and 0.25 mg/ml acepromazine and isolated mouse lungs were prepared and perfused as described.[20] All lung preparations underwent a 20 min equilibration perfusion, and lungs that were not isogravimetric at the end of this period were discarded. After a 20-min equilibration perfusion, outflow pressure was elevated by 10 cm $H_2O$ for 2 min. The lung wet weight increase over this time, which reflects the net fluid accumulation, was continuously recorded. At the end of each experiment, lung dry weight was determined. $K_{f,c}$ (ml·min$^{-1}$·cm$H_2O$·g dry wt$^{-1}$) was calculated from the slope of the recorded weight change normalized to the pressure change and lung dry weight. The expression of MLCL-L in lungs was determined by Western blotting of lung homogenate with anti-MLCK Ab.

Transfection of siRNA siRNAs were transfected into cells using Santa Cruz transfection reagent following manufacture's protocol.

Western Blotting

Lysates from HPAE cell monolayers were Western blotted with indicated antibodies using published protocols.[21]

Cytosolic $Ca^{2+}$ Measurements

An increase in intracellular $Ca^{2+}$ was measured using the $Ca^{2+}$-sensitive fluorescent dye Fura 2-AM as described.[21, 22]

Measurements of RhoA Activity

RhoA activity was measured using GST-rhotekin-Rho binding domain (GST-RBD) that specifically pulls down activated RhoA as described.[21, 22]

Immunoflorescence

After stimulation with thrombin, cells were rinsed quickly with ice-cold HBSS, fixed and stained with anti-VE-cadherin Ab followed by alexa-labeled secondary Ab as described previously.[21]

MLC Phosphorylation

Cells stimulated with thrombin were lysed with Laemmli sample buffer and western blotted with antibodies for phosphorylated-MLC or pan-MLC Abs to determine MLC phosphorylation.

Transendothelial Electrical Resistance Measurement

The time course of endothelial cell retraction, a measure of increased endothelial permeability, was measured using established protocols.[23]

Statistical Analysis

Two-tailed Student t-test and one-way ANOVA with Bonferroni post-hoc test were used for statistical comparisons. Differences were considered significant at $P<0.05$.

Example 2

MLCK-L Knockdown Prevents MLC Phosphorylation Without Altering RhoA Activation

Three siRNA sequences corresponding to the N-terminal region of MLCK-L were constructed. Western blot analysis showed that siRNA Seq 3 reduced MLCK-L expression by ~75% within 48 hr (FIG. 1A-B). Seq 1, by contrast, was ineffective (FIG. 1A-B). Thus, in the remainder of the study, we used Seq 1 as control for comparison with Seq 3 (i.e. MLCK-L siRNA) to address the role of MLCK-L in regulating endothelial barrier function. Thrombin induced MLC phosphorylation in cells transfected with control siRNA (FIG. 2). However, "knockdown" of MLCK-L prevented MLC phosphorylation (FIG. 2A-B). A recent study showed that Rho kinase can also phosphorylate MLC.[24] To see if the observed inhibition of MLC phosphorylation is due to altered RhoA-Rho kinase activity in MLCK-L knock-down cells, we performed a Rho activity assay and also determined phosphorylation of MYTP-1, a specific Rho kinase substrate. Thrombin induced equivalent RhoA activation in control and in MLCK-L knockdown cells (FIG. 3A). We determined the extent of MYPT1 phosphorylation using an anti-phospho-thr850 MYPT1 antibody. Suppression of MLCK-L had no effect on thrombin-induced MYPT1 phosphorylation (FIG. 3B-C). Thus, these results indicate the essential role of MLCK-L in inducing MLC phosphorylation independently of the Rho/Rho kinase pathway.

Example 3

Impaired Ca2+ Influx in MLCK-L Knock-Down Endothelial Cells in Response to Thrombin or Thapsigargin We investigated whether calcium entry calcium entry through store-operated channels (required for endothelial monolayer retraction) is impaired in MLCK-deficient endothelial cells. We therefore determined whether suppression of endogenous MLCK-L affects store-operated calcium entry channels (SOCs) in Fura-2 loaded endothelial monolayer. We used thrombin to deplete the ER calcium store and elicit calcium entry. We separately assessed the calcium-release and calcium-entry components using a $Ca^{2+}$ add-back protocol, which allowed us to determine the role of MLCK-L in regulating SOC activation. We observed that under $Ca^{2+}$-free bath conditions, MLCK-L knockdown had no effect on thrombin-induced release of $Ca^{2+}$ from stores (FIG. 4A-B). However, suppression of MLCK-L expression significantly reduced $Ca^{2+}$ entry upon bath-calcium repletion (FIG. 4A-B).

We used thapsigargin for comparison with thrombin, since thapsigargin activates SOCs independently of ligand-receptor-G protein-coupled receptors. Thapsigargin increased $Ca^{2+}$ entry via SOCs (FIG. 4C-D), as expected. However, suppression of MLCK-L inhibited SOC activation (FIG. 4C-D). These findings thereby indicate that MLCK-L regulates SOC channels independently of G-protein signaling downstream of the PAR-1 receptor.

Example 4

MLCK-L Knockdown Prevents Cell Retraction in Response to Thrombin

Since our studies show that MLCK-L deficiency led to suppression of thrombin-induced calcium entry and MLC phosphorylation, we next measured endothelial cell retraction and paracellular permeability increase in response to thrombin. We determined adherens junction organization to assess the effect of MLCK-L knock-down on thrombin-induced junctional disassembly, a prerequisite for the increase in endothelial permeability. We also determined transendothelial electrical resistance (TER) in endothelial monolayers to address the role of MLCK-L in regulating endothelial permeability. As shown in FIG. 5, thrombin induced the disruption of adherens junction in cells transfected with control siRNA. However, this response was not seen in cells transfected with MLCK-L siRNA. In endothelial monolayers transfected with control siRNA, thrombin caused a decrease in transendothelial monolayer electrical resistance of ≈55% (FIG. 6). By contrast, exposure of thrombin to MLCK-L knockdown cells produced only a ≈15% decrease in resistance after thrombin challenge (FIG. 6). Thus, these findings identify the specific role of MLCK-L as a key regulator of endothelial barrier function in response to thrombin.

Example 5

Deletion of MLCK-L in Mice Prevents Increase in Lung Vascular Permeability in Response to Selective PAR-1 Receptor Agonist TFLLRNPNDK (SEQ ID NO: 5)

We measured microvessel liquid permeability in isolated lung preparations from wild-type (WT) and MLCK-L$^{-/-}$ mice to determine the role of MLCK-L in regulating lung vascular permeability (FIG. 7A, inset). We found that basal values of $K_{f,c}$ did not significantly differ between WT and MLCK-L$^{-/-}$ lungs (FIG. 7A). In wt mice, PAR-1 activation produced a 2-3-fold increase in lung $K_{f,c}$ within 15 minutes (FIG. 7A). However, this response was not observed in lungs from MLCK-L$^{-/-}$ mice. We also determined PAR-1-induced pulmonary vasoconstriction in the MLCK-L$^{-/-}$ mice. Thrombin-induced vasoconstriction was the same in MLCK-L$^{-/-}$ mouse lung as in the WT mice lung. Thus, these results identify the specific role of MLCK-L$^{-/-}$ in the mechanism of endothelial permeability increase in contrast to the other isoform specific to vascular smooth muscle cells, which mediates vasoconstriction (FIG. 7B).

We next determined the effect of thrombin on the extent of MLC phosphorylation in mouse lung tissue pretreated with PAR-1 agonist to address the possibility that the impairment in lung vascular permeability is the result of inhibition of MLC phosphorylation. Western immunoblots show MLC and phosphorylated MLC (FIG. 8). In lung tissue obtained from normal mice, thrombin induced an increase in MLC phosphorylation. Induction of MLC phosphorylation by thrombin was decreased in lung tissue taken from MLCK-L null mice, indicating the essential role of MLC phosphorylation induced by MLCK-L in mediating the thrombin action.

Example 6

Reduction in Eye Inflammation

We observed a significant inhibition of the eye inflammation in the mouse lacking the MLCK gene. Wild type or MLCK-L knockout mice were anesthetized following protocol approved by UIC Animal Care Committee. The subconjunctival scarring was generated by injecting 30 μl of PBS containing latex beads in the temporal subconjunctival space of the mouse's left eye. The beads were 1.053 μm in diameter, 300 μg/ml (Polyscience, Warrington, Pa.). The right eye, which received no injection, served as an internal control in each group. One-week post treatment mice were sacrificed by cervical dislocation. Eyes were removed by enucleation and fixed in 10% buffered folinalin and 5 μm thick paraffin sections were prepared. The sections were stained with hematoxylin and eosin to assess the inflammatory reaction and picrocirius red to visualize the collagen deposit. The numbers of inflammatory cells in subconjunctival areas in the sections were counted. The value was normalized to the number of inflammatory cells per unit area (2500 μm²) underneath the conjunctival epithelium. For each treatment at least 4 mice were used. See FIG. 9.

Example 10

Suppression of Endogenous MLCK-L in Mice Events LPS-Induced Lung Injury

We used MLCK siRNA to address the possibility that knockdown of MLCK-L protects mouse against LPS, a bacterial endotoxin, induced lung injury. As shown in FIG. 1, transduction of MLCK-L siRNA (but not control siRNA) decreased MLCK-L (210) but not smooth muscle isoform (130) expression after 48 hr of transfection. We observed that in mice injected with control siRNA, administration of LPS induced a marked increase in lung inflammation as indicated by changes in the lung wet- to dry weight ratio, albumin accumulation in the lung and increased number of inflammatory cells in the bronchoalveolar lavage of mice. However, LPS-induced lung injury was significantly reduced in mice injected with MLCK-L siRNA. See FIG. 10.

REFERENCES

Publications (references) cited herein and the material for which they are cited are specifically incorporated by reference. Nothing herein is to be construed as an admission that the publication is prior art to the invention herein disclosed and claimed, or that the publications bear negatively on patentability of the same, or that the invention is not entitled to antedate any such reference.

1. Mehta D, Malik A B. Signaling mechanisms regulating endothelial permeability. *Physiol Rev.* January 2006; 86(1):279-367.
2. Majno G, Palade G E. Studies on inflammation. 1. The effect of histamine and serotonin on vascular permeability: an electron microscopic study. *J Biophys Biochem Cytol.* December 1961; 11:571-605.
3. Dudek S M, Garcia J G. Cytoskeletal regulation of pulmonary vascular permeability. *J Appl Physiol.* October 2001; 91(4):1487-1500.
4. Wysolmerski R B, Lagunoff D. Involvement of myosin light-chain kinase in endothelial cell retraction. *Proc Natl Acad Sci USA.* January 1990; 87(1):16-20,
5. Wysolmerski R B, Lagunoff D. Regulation of permeabilized endothelial cell retraction by myosin phosphorylation. *Am J Physiol.* July 1991; 261(1 Pt 1):C32-40.
6. Wainwright M S, Rossi J, Schavocky J, et al. Protein kinase involved in lung injury susceptibility: evidence from enzyme isoform genetic knockout and in vivo inhibitor treatment. *Proc Natl Acad Sci USA.* May 13, 2003; 100 (10):6233-6238.
7. Tinsley J H, De Lanerolle P, Wilson E, et al. Myosin light chain kinase transference induces myosin light chain activation and endothelial hyperpermeability. *Am J Physiol Cell Physiol.* October 2000; 279(4):C1285-1289.
8. Garcia J G, Davis H W, Patterson C E. Regulation of endothelial cell gap formation and barrier dysfunction: role of myosin light chain phosphorylation. *J Cell Physiol.* June 1995; 163(3):510-522.
9. Garcia J G, Lazar V, Gilbert-McClain L I, et al. Myosin light chain kinase in endothelium: molecular cloning and regulation. *Am J Respir Cell Mol Biol.* May 1997; 16(5): 489-494.
10. Khimenko P L, Moore T M, Wilson P S, et al. Role of calmodulin and myosin light-chain kinase in lung ischemia-reperfusion injury. *Am J Physiol.* July 1996; 271(1 Pt 1):L121-125.
11. Garcia J G, Verin A D, Herenyiova M, et al. Adherent neutrophils activate endothelial myosin light chain kinase: role in transendothelial migration. *J Appl Physiol.* May 1998; 84(5):1817-1821.
12. Saito H, Minamiya Y, Kitamura M, et al. Endothelial myosin light chain kinase regulates neutrophil migration across human umbilical vein endothelial cell monolayer. *J Immunol.* Aug. 1, 1998; 161(3):1533-1540.
13. Lazar V, Garcia J G. A single human myosin light chain kinase gene (MLCK; MYLK). *Genomics.* Apr. 15, 1999; 57(2):256-267.
14. Gao L, Grant A, Halder I, et al. Novel polymorphisms in the myosin light chain kinase gene confer risk for acute lung injury. *Am J Respir Cell Mol Biol.* April 2006; 34(4): 487-495.
15. Verin A D, Gilbert-McClain L I, Patterson C E, et al. Biochemical regulation of the nonmuscle myosin light chain kinase isoform in bovine endothelium. *Am J Respir Cell Mol Biol.* November 1998; 19(5):767-776.
16. Verin A D, Lazar V, Torry R J, et al. Expression of a novel high molecular-weight myosin light chain kinase in endothelium. *Am J Respir Cell Mol Biol.* November 1998; 19(5): 758-766.
17. Blue E K, Goeckeler Z M, Jin Y, et al. 220- and 130-kDa MLCKs have distinct tissue distributions and intracellular localization patterns. *Am J Physiol Cell Physiol.* March 2002; 282(3):C451-460.
18. Wadgaonkar R, Dudek S M, Zaiman A L, et al. Intracellular interaction of myosin light chain kinase with macrophage migration inhibition factor (MIF) in endothelium. *J Cell Biochem.* Jul. 1, 2005; 95(4):849-858.
19. Kudryashov D S, Stepanova O V, Vilitkevich E L, et al. Myosin light chain kinase (210 kDa) is a potential cytoskeleton integrator through its unique N-terminal domain. *Exp Cell Res.* Aug. 15, 2004; 298(2):407-417.
20. Vogel S M, Gao X, Mehta D, et al. Abrogation of thrombin-induced increase in pulmonary microvascular permeability in PAR-1 knockout mice. *Physiol Genomics.* Dec. 18, 2000; 4(2):137-145.
21. Mehta D, Ahmmed G U, Pana B C, et al. RhoA interaction with inositol 1,4,5-trisphosphate receptor and transient receptor potential channel-1 regulates Ca2+ entry. Role in signaling increased endothelial permeability. *J Biol Chem.* Aug. 29, 2003; 278(35):33492-33500.
22. Ahmmed G U, Mehta D, Vogel S, et al. Protein kinase Calpha phosphorylates the TRPC1 channel and regulates store-operated Ca2+ entry in endothelial cells. *J Biol Chem.* May 14, 2004; 279(20):20941-20949.
23. Tiruppathi C, Malik A B, Del Vecchio P J, et al. Electrical method for detection of endothelial cell shape change in real time: assessment of endothelial barrier function. *Proc Natl Acad Sci USA.* Sep. 1, 1992; 89(17):7919-7923.
24. Emmert D A, Fee J A, Goeckeler Z M, et al. Rho-kinase-mediated Ca2+-independent contraction in rat embryo fibroblasts. *Am J Physiol Cell Physiol.* January 2004; 286 (1):C8-21.
25. Moore T, Brough G, Kelly J, et al. Regulation of pulmonary endothelial cell shape by Trp-mediated calcium entry. *Chest.* July 1998; 114(1 Suppl):36S-38S.

26. Moore T M, Brough G H, Babal P, et al. Store-operated calcium entry promotes shape change in pulmonary endothelial cells expressing Trp1. *Am J Physiol*. September 1998; 275(3 Pt 1):L574-582.
27. Moore T M, Norwood N R, Creighton J R, et al. Receptor-dependent activation of store-operated calcium entry increases endothelial cell permeability. *Am J Physiol Lung Cell Mol Physiol*. October 2000; 279(4):L691-698.
28. Nilius B, Droogmans G. Ion channels and their functional role in vascular endothelium. *Physiol Rev*. October 2001; 81(4):1415-1459.
29. Tiruppathi C, Freichel M, Vogel S M, et al. Impairment of store-operated Ca2+ entry in TRPC4(−/−) mice interferes with increase in lung microvascular. *Circ Res*. Jul. 12, 2002; 91(1):70-76.
30. Paria B C, Vogel S M, Ahmmed G U, et al. Tumor necrosis factor-alpha-induced TRPC1 expression amplifies store-operated Ca2+ influx and endothelial permeability. *Am J Physiol Lung Cell Mol Physiol*. December 2004; 287(6): L1303-1313.
31. Watanabe H, Tran Q K, Takeuchi K, et al. Myosin light-chain kinase regulates endothelial calcium entry and endothelium-dependent vasodilation. *Faseb J*. February 2001; 15(2):282-284.
32. Shimizu S, Yoshida T, Wakamori M, et al. Ca2+-calmodulin-dependent myosin light chain kinase is essential for activation of TRPC5 channels expressed in HEK293 cells. *J Physiol*. Jan. 15, 2006; 570(Pt 2):219-235.
33. Ohlmann P, Tesse A, Loichot C, et al. Deletion of MLCK210 induces subtle changes in vascular reactivity but does not affect cardiac function. *Am J Physiol Heart Circ Physiol*. December 2005; 289(6):H2342-2349.

What is claimed is:

1. A double-stranded siRNA that directs cleavage of a myosin light chain kinase (MLCK) RNA, wherein
   (a) each strand of said siRNA molecule is about 19 to about 25 nucleotides in length;
   (b) one strand of said siRNA molecule comprises a region having a nucleotide sequence having sufficient complementarity to a MLCK RNA for the siRNA molecule to direct cleavage of the MLCK RNA via RNA interference;
   (c) the siRNA comprises a region having the sequence of SEQ ID NO:3; and
   (d) the siRNA specifically cleaves MLCK-L RNA and substantially does not cleave MLCK-S RNA.

2. A method for modulating MLCK expression in a cell, comprising introducing into a cell a double stranded siRNA that cleaves MLCK RNA, wherein
   (a) each strand of said siRNA molecule is about 19 to about 25 nucleotides in length;
   (b) one strand of said siRNA molecule comprises a region having a nucleotide sequence having sufficient complementarity to the MLCK RNA for the siRNA molecule to direct cleavage of the MLCK RNA via RNA interference;
   (c) the siRNA comprises a region having the sequence of SEQ ID NO:3; and
   (d) the siRNA specifically cleaves MLCK-L RNA and substantially does not cleave MLCK-S RNA.

3. A method for modulating tissue inflammation in a patient suffering therefrom, comprising administering to a patient suffering from tissue inflammation a siRNA in an amount and by a route effective to modulate said tissue inflammation, wherein the siRNA is a double stranded siRNA wherein
   (a) each strand of the siRNA molecule is about 19 to about 25 nucleotides in length;
   (b) one strand of the siRNA molecule comprises a region having sufficient complementarity to an RNA encoded by a MLCK gene for the siRNA molecule to direct specific cleavage of the MLCK-L RNA via RNA interference and not substantially cleave MLCK-S RNA; and
   (c) the siRNA comprises a region having the sequence of SEQ ID NO:3.

4. A method for treating asthma in a patient suffering therefrom, comprising administering to a patient suffering from asthma a siRNA in an amount and by a route effective to treat asthma, wherein the siRNA is a double stranded siRNA wherein
   (a) each strand of the siRNA molecule is about 19 to about 25 nucleotides in length;
   (b) one strand of the siRNA molecule comprises a region having sufficient complementarity to an RNA encoded by a MLCK gene for the siRNA molecule to direct specific cleavage of the MLCK-L RNA via RNA interference and not substantially cleave MLCK-S RNA; and
   (c) the siRNA comprises a region having the sequence of SEQ ID NO:3.

* * * * *